(12) United States Patent
Johnson

(10) Patent No.: US 8,324,218 B2
(45) Date of Patent: Dec. 4, 2012

(54) ALIPHATIC PYRAZINOYLGUANIDINE SODIUM CHANNEL BLOCKERS WITH BETA AGONIST ACTIVITY

(75) Inventor: Michael Ross Johnson, Chapel Hill, NC (US)

(73) Assignee: Parion Sciences, Inc., Durham, NC (US)

( * ) Notice: Subject to any disclaimer, the term of this patent is extended or adjusted under 35 U.S.C. 154(b) by 196 days.

(21) Appl. No.: 12/304,040

(22) PCT Filed: Jun. 11, 2007

(86) PCT No.: PCT/US2007/070857
§ 371 (c)(1),
(2), (4) Date: Jun. 23, 2010

(87) PCT Pub. No.: WO2007/146867
PCT Pub. Date: Dec. 21, 2007

(65) Prior Publication Data
US 2010/0267746 A1    Oct. 21, 2010

Related U.S. Application Data

(60) Provisional application No. 60/812,078, filed on Jun. 9, 2006.

(51) Int. Cl.
*A61K 31/4965* (2006.01)
(52) U.S. Cl. .................. 514/255.06; 544/409
(58) Field of Classification Search ............. 514/255.06; 544/409
See application file for complete search history.

(56) References Cited

U.S. PATENT DOCUMENTS

| | | |
|---|---|---|
| 6,858,614 B2 | 2/2005 | Johnson |
| 6,858,615 B2 | 2/2005 | Johnson |
| 6,903,105 B2 | 6/2005 | Johnson |
| 6,995,160 B2 | 2/2006 | Johnson |
| 7,026,325 B2 | 4/2006 | Johnson |
| 7,030,117 B2 | 4/2006 | Johnson |
| 7,064,129 B2 | 6/2006 | Johnson et al. |
| 7,186,833 B2 | 3/2007 | Johnson |
| 7,189,719 B2 | 3/2007 | Johnson |
| 7,192,958 B2 | 3/2007 | Johnson |
| 7,192,959 B2 | 3/2007 | Johnson |
| 7,192,960 B2 | 3/2007 | Johnson |
| 7,241,766 B2 | 7/2007 | Johnson |
| 7,247,636 B2 | 7/2007 | Johnson |
| 7,247,637 B2 | 7/2007 | Johnson et al. |
| 7,317,013 B2 | 1/2008 | Johnson |
| 7,332,496 B2 | 2/2008 | Johnson |
| 7,345,044 B2 | 3/2008 | Johnson |
| 7,368,447 B2 | 5/2008 | Johnson et al. |
| 7,368,450 B2 | 5/2008 | Johnson |
| 7,368,451 B2 | 5/2008 | Johnson et al. |
| 7,375,107 B2 | 5/2008 | Johnson |
| 7,388,013 B2 | 6/2008 | Johnson et al. |
| 7,399,766 B2 | 7/2008 | Johnson |
| 7,410,968 B2 | 8/2008 | Johnson et al. |
| 2005/0080092 A1 | 4/2005 | Johnson |
| 2005/0080093 A1 | 4/2005 | Johnson et al. |
| 2005/0090505 A1 | 4/2005 | Johnson et al. |
| 2006/0142306 A1 | 6/2006 | Johnson |
| 2006/0142581 A1 | 6/2006 | Johnson |
| 2007/0032509 A1 | 2/2007 | Johnson et al. |
| 2007/0265280 A1 | 11/2007 | Johnson |
| 2008/0076782 A1 | 3/2008 | Johnson |
| 2008/0090841 A1 | 4/2008 | Johnson et al. |
| 2008/0096896 A1 | 4/2008 | Johnson |
| 2008/0103148 A1 | 5/2008 | Johnson |
| 2008/0167466 A1 | 7/2008 | Johnson et al. |
| 2008/0171879 A1 | 7/2008 | Johnson |
| 2008/0171880 A1 | 7/2008 | Johnson et al. |
| 2008/0176863 A1 | 7/2008 | Johnson et al. |
| 2008/0177072 A1 | 7/2008 | Johnson |
| 2008/0200476 A1 | 8/2008 | Johnson |
| 2008/0249109 A1 | 10/2008 | Johnson et al. |
| 2008/0293740 A1 | 11/2008 | Johnson et al. |

FOREIGN PATENT DOCUMENTS
WO    WO 2007/146867    * 12/2007

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
U.S. Appl. No. 12/393,252, filed Feb. 26, 2009, Johnson.
Strosberg, A. "Structure and Function of the β3-Adrenergic Receptor", Annu. Rev. Pharmacol. Toxicol., vol. 37, pp. 421-450, (1997).

(Continued)

*Primary Examiner* — Douglas M Willis
(74) *Attorney, Agent, or Firm* — Oblon, Spivak, McClelland, Maier & Neustadt, L.L.P.

(57) ABSTRACT

The present application provides sodium channel blockers exemplified by the following structure:

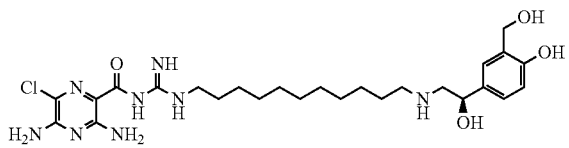

The compounds of the invention useful for treating chronic bronchitis, cystic fibrosis, sinusitis, vaginal dryness, dry eye, Sjogren's disease, distal intestinal obstruction syndrome, dry skin, esophagitis, dry mouth (xerostomia), nasal dehydration, ventilator-induced pneumonia, asthma, primary ciliary dyskinesia, otitis media, chronic obstructive pulmonary disease, emphysema, pneumonia, constipation, and chronic diverticulitis, for example.

3 Claims, 4 Drawing Sheets

OTHER PUBLICATIONS

Shryock, JC. et al. "Adenosine and adenosine receptors in the cardiovascular system:", Biochemistry, Physiology and Pharmacology, vol. 79, pp. 2-10, (1997) (English abstract).
U.S. Appl. No. 13/353,018, filed Jan. 18, 2012, Johnson.
U.S. Appl. No. 60/909,082, filed Apr. 3, 2007, Johnson, et al.
U.S. Appl. No. 12/501,654, filed Jul. 13, 2009, Boucher, et al.
U.S. Appl. No. 12/939,579, filed Nov. 4, 2010, Johnson, et al.
U.S. Appl. No. 12/876,615, filed Sep. 7, 2010, Johnson, et al.
U.S. Appl. No. 10/920,527, filed Aug. 18, 2004, Hopkins.
U.S. Appl. No. 60/495,725, filed Aug. 18, 2003, Johnson.
U.S. Appl. No. 60/495,720, filed Aug. 18, 2003, Johnson.
U.S. Appl. No. 60/495,712, filed Aug. 18, 2003, Johnson.
U.S. Appl. No. 60/602,312, filed Aug. 18, 2004, Johnson.
U.S. Appl. No. 60/602,327, filed Aug. 18, 2004, Johnson.
U.S. Appl. No. 60/812,091, filed Jun. 9, 2006, Johnson.
U.S. Appl. No. 60/812,077, filed Jun. 9, 2006, Johnson, et al.
U.S. Appl. No. 60/812,078, filed Jun. 9, 2006, Johnson.
U.S. Appl. No. 60/842,669, filed Sep. 7, 2006, Johnson, et al.
U.S. Appl. No. 60/842,963, filed Sep. 8, 2006, Johnson, et al.
U.S. Appl. No. 60/845,171, filed Sep. 18, 2006, Johnson, et al.
U.S. Appl. No. 11/696,003, filed Apr. 3, 2007, Johnson.
U.S. Appl. No. 11/573,413, filed Feb. 8, 2007, Johnson.
U.S. Appl. No. 11/573,421, filed Feb. 8, 2007, Johnson.
U.S. Appl. No. 60/909,818, filed Apr. 3, 2007, Johnson, et al.
U.S. Appl. No. 11/852,003, filed Sep. 7, 2007, Johnson, et al.
U.S. Appl. No. 60/978,887, filed Oct. 10, 2007, Boucher, et al.
U.S. Appl. No. 60/978,874, filed Oct. 10, 2007, Boucher, et al.
U.S. Appl. No. 60/987,663, filed Nov. 13, 2007, Johnson, et al.
U.S. Appl. No. 61/013,387, filed Dec. 13, 2007, Johnson, et al.
U.S. Appl. No. 11/835,902, filed Aug. 8, 2007, Johnson, et al.
U.S. Appl. No. 61/030,313, filed Feb. 21, 2008, Johnson.
U.S. Appl. No. 61/031,466, filed Feb. 26, 2008, Johnson.
U.S. Appl. No. 12/049,993, filed Mar. 17, 2008, Johnson.
U.S. Appl. No. 12/171,814, filed Jul. 11, 2008, Johnson, et al.
U.S. Appl. No. 12/171,867, filed Jul. 11, 2008, Johnson, et al.
U.S. Appl. No. 12/171,897, filed Jul. 11, 2008, Johnson, et al.
U.S. Appl. No. 12/190,022, filed Aug. 12, 2008, Johnson.
U.S. Appl. No. 61/079,989, filed Jul. 11, 2008, Boucher, et al.
U.S. Appl. No. 12/179,353, filed Jul. 24, 2008, Johnson.
U.S. Appl. No. 12/249,175, filed Oct. 10, 2008, Boucher, et al.
U.S. Appl. No. 12/304,006, filed Dec. 9, 2008, Johnson, et al.
U.S. Appl. No. 12/304,042, filed Dec. 9, 2008, Johnson.
U.S. Appl. No. 12/304,040, filed Dec. 9, 2008, Johnson.

* cited by examiner

Figure 4: Tautomeric Forms of Formula I Compounds
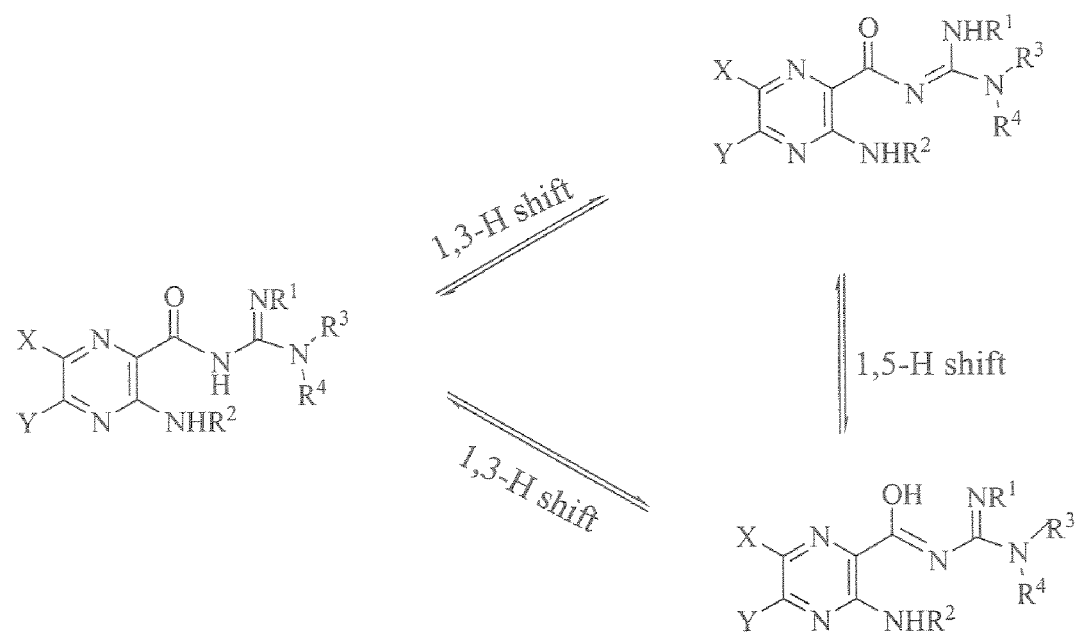

ALIPHATIC PYRAZINOYLGUANIDINE SODIUM CHANNEL BLOCKERS WITH BETA AGONIST ACTIVITY

CONTINUING APPLICATION DATA

This application is a National Stage of International application No. PCT/US07/70857, filed on Jun. 11, 2007, incorporated herein by reference; which claims priority to U.S. provisional application Ser. No. 60/812,078, filed on Jun. 9, 2006, and incorporated herein by reference.

BACKGROUND OF THE INVENTION

1. Field of the Invention

The present invention relates to sodium channel blockers possessing beta-adrenergic receptor agonist activity. The present invention also includes a variety of methods of treatment using these inventive sodium channel blockers/beta-adrenergic receptor agonists.

2. Description of the Background

The mucosal surfaces at the interface between the environment and the body have evolved a number of "innate defenses", i.e., protective mechanisms. A principal form of such an innate defense is to cleanse these surfaces with liquid. Typically, the quantity of the liquid layer on a mucosal surface reflects the balance between epithelial liquid secretion, often reflecting anion ($Cl^-$ and/or $HCO_3^-$) secretion coupled with water (and a cation counter-ion), and epithelial liquid absorption, often reflecting $Na^+$ absorption, coupled with water and counter anion ($Cl^-$ and/or $HCO_3^-$). Many diseases of mucosal surfaces are caused by too little protective liquid on those mucosal surfaces created by an imbalance between secretion (too little) and absorption (relatively too much). The defective salt transport processes that characterize these mucosal dysfunctions reside in the epithelial layer of the mucosal surface.

One approach to replenish the protective liquid layer on mucosal surfaces is to "re-balance" the system by blocking $Na^+$ channel and liquid absorption and simultaneously activating beta-adrenergic receptors thereby causing liquid secretion. The epithelial protein that mediates the rate-limiting step of $Na^+$ and liquid absorption is the epithelial $Na^+$ channel (ENaC). ENaC and beta-adrenergic receptors are positioned on the apical surface of the epithelium, i.e. the mucosal surface-external environment interface. Therefore, to inhibit ENaC mediated $Na^+$ and liquid absorption, an ENaC blocker of the amiloride class (which blocks from the extracellular domain of ENaC) must be delivered to the mucosal surface and, importantly, be maintained at this site, to achieve therapeutic utility. The present invention describes diseases characterized by too little liquid on mucosal surfaces and "topical" sodium channel blockers containing beta-adrenergic receptor agonist activity designed to exhibit the increased potency, reduced mucosal absorption, and slow dissociation ("unbinding" or detachment) from ENaC and the beta-adrenergic receptor required for therapy of these diseases.

Chronic bronchitis (CB), including the most common lethal genetic form of chronic bronchitis, cystic fibrosis (CF), are diseases that reflect the body's failure to clear mucus normally from the lungs, which ultimately produces chronic airways infection. In the normal lung, the primary defense against chronic intrapulmonary airways infection (chronic bronchitis) is mediated by the continuous clearance of mucus from bronchial airway surfaces. This function in health subjects effectively removes from the lung potentially noxious toxins and pathogens. Recent data indicate that the initiating problem, i.e., the "basic defect," in both CB and CF is the failure to clear mucus from airway surfaces. The failure to clear mucus reflects an imbalance between the amount of liquid and mucin on airway surfaces. This "airway surface liquid" (ASL) is primarily composed of salt and water in proportions similar to plasma (i.e., isotonic). Mucin macromolecules are organized into a well defined "mucus layer" which normally traps inhaled bacteria and are transported out of the lung via the actions of cilia which beat in a watery, low viscosity solution termed the "periciliary liquid" (PCL). In the disease state, there is an imbalance in the quantities of mucus and ASL on airway surfaces. This imbalance results in a relative reduction in ASL which leads to mucus concentration, a reduction in the lubricant activity of the PCL, and a failure to clear mucus via ciliary activity to the mouth. The reduction in mechanical clearance of mucus from the lung leads to chronic bacterial colonization of mucus adherent to airway surfaces. It is the chronic retention of bacteria, the failure of local antimicrobial substances to kill mucus-entrapped bacteria on a chronic basis, and the consequent chronic inflammatory responses of the body to this type of surface infection, that lead to the syndromes of CB and CF.

The current afflicted population in the U.S. is 12,000,000 patients with the acquired (primarily from cigarette smoke exposure) form of chronic bronchitis and approximately 30,000 patients with the genetic form, cystic fibrosis. Approximately equal numbers of both populations are present in Europe. In Asia, there is little CF but the incidence of CB is high and, like the rest of the world, is increasing.

There is currently a large, unmet medical need for products that specifically treat CB and CF at the level of the basic defect that cause these diseases. The current therapies for chronic bronchitis and cystic fibrosis focus on treating the symptoms and/or the late effects of these diseases. Thus, for chronic bronchitis, inhaled β-agonists, steroids, anti-cholinergic agents, and oral theophyllines and phosphodiesterase inhibitors are all in current use. However, none of these drugs alone effectively treat the fundamental problem of the failure to clear mucus from the lung. Similarly, in cystic fibrosis, the same spectrum of pharmacologic agents are used. These strategies have been complemented by more recent strategies designed to clear the CF lung of the DNA ("Pulmozyme"; Genentech) that has been deposited in the lung by neutrophils that have futilely attempted to kill the bacteria that grow in adherent mucus masses and through the use of inhaled antibiotics (e.g. "TOBI") designed to augment the lungs' own killing mechanisms to rid the adherent mucus plaques of bacteria. A general principle of the body is that if the initiating lesion is not treated, in this case mucus retention/obstruction, bacterial infections become chronic and increasingly refractory to antimicrobial therapy. Thus, a major unmet therapeutic need for both CB and CF lung diseases is an effective means of re-hydrating airway mucus (i.e., restoring/expanding the volume of the ASL) and promoting its clearance, with bacteria, from the lung.

R. C. Boucher, in U.S. Pat. No. 6,264,975, describes the use of pyrazinoylguanidine sodium channel blockers for hydrating mucosal surfaces. These compounds, typified by the well-known diuretics amiloride, benzamil, and phenamil, are effective. However, these compounds suffer from the significant disadvantage that they are (1) relatively impotent, which is important because the mass of drug that can be inhaled by the lung is limited; (2) rapidly absorbed, which limits the half-life of the drug on the mucosal surface; and (3) are freely dissociable from ENaC. The sum of these disadvantages embodied in these well known diuretics produces compounds with insufficient potency and/or effective half-life on mucosal surfaces to have therapeutic benefit for hydrating mucosal surfaces.

Clearly, what is needed are drugs that are more effective at restoring the clearance of mucus from the lungs of patients with CB/CF. The value of these new therapies will be reflected in improvements in the quality and duration of life for both the CF and the CB populations.

Other mucosal surfaces in and on the body exhibit subtle differences in the normal physiology of the protective surface liquids on their surfaces but the pathophysiology of disease reflects a common theme, i.e., too little protective surface liquid. For example, in xerostomia (dry mouth) the oral cavity is depleted of liquid due to a failure of the parotid sublingual and submandibular glands to secrete liquid despite continued $Na^+$ (ENaC) transport mediated liquid absorption from the oral cavity. Similarly, keratoconjunctivitis sira (dry eye) is caused by failure of lacrimal glands to secrete liquid in the face of continued $Na^+$ dependent liquid absorption on conjunctional surfaces. In rhinosinusitis, there is an imbalance, as in CB, between mucin secretion and relative ASL depletion. Finally, in the gastrointestinal tract, failure to secrete Cl— (and liquid) in the proximal small intestine, combined with increased $Na^+$ (and liquid) absorption in the terminal ileum leads to the distal intestinal obstruction syndrome (DIOS). In older patients, excessive $Na^+$ (and volume) absorption in the descending colon produces chronic constipation and diverticulitis.

SUMMARY OF THE INVENTION

It is an object of the present invention to provide compounds that have both sodium channel blocking activity and beta-adrenergic receptor agonist activity in the same molecule.

It is an object of the present invention to provide compounds that are more potent and/or absorbed less rapidly from mucosal surfaces, and/or are less reversible as compared to known compounds.

It is another aspect of the present invention to provide compounds that are more potent and/or absorbed less rapidly and/or exhibit less reversibility, as compared to compounds such as amiloride, benzamil, and phenamil. Therefore, the compounds will give a prolonged pharmacodynamic half-life on mucosal surfaces as compared to known compounds.

It is another object of the present invention to provide compounds which are (1) absorbed less rapidly from mucosal surfaces, especially airway surfaces, as compared to known compounds and; (2) when absorbed from mucosal surfaces after administration to the mucosal surfaces, are converted in vivo into metabolic derivatives thereof which have reduced efficacy in blocking sodium channels and beta-adrenergic receptor agonist activity as compared to the administered parent compound.

It is another object of the present invention to provide compounds that are more potent and/or absorbed less rapidly and/or exhibit less reversibility, as compared to compounds such as amiloride, benzamil, and phenamil. Therefore, such compounds will give a prolonged pharmacodynamic half-life on mucosal surfaces as compared to previous compounds.

It is another object of the present invention to provide methods of treatment that take advantage of the pharmacological properties of the compounds described above.

In particular, it is an object of the present invention to provide methods of treatment which rely on rehydration of mucosal surfaces.

Any of the compounds described herein can be a pharmaceutically acceptable salt thereof, and wherein the above compounds are inclusive of all racemates, enantiomers, diastereomers, tautomers, polymorphs and pseudopolymorphs thereof. Polymorphs are different physical forms—different crystal forms that have differing melting ranges, show differing differential scanning calorimetry (DSC) tracings and exhibit different X-Ray powder diffraction (XRPD) spectra. Pseudopolymorphs are different solvated physical forms—different crystal forms that have differing melting ranges as solvates, show differing differential scanning calorimetry (DSC) tracings as solvates and exhibit different X-Ray powder diffraction (XRPD) spectra as solvates.

The present invention also provides pharmaceutical compositions which contain a compound described above.

The present invention also provides a method of promoting hydration of mucosal surfaces, comprising:

administering an effective amount of a compound represented by formula (I) to a mucosal surface of a subject.

The present invention also provides a method of restoring mucosal defense, comprising:

topically administering an effective amount of compound represented by formula (I) to a mucosal surface of a subject in need thereof.

The present invention also provides a method of blocking ENaC and exerting beta-adrenergic receptor agonism comprising:

contacting sodium channels and at the same time activating beta-adrenergic receptors (beta agonists) with an effective amount of a compound represented by formula (I).

The objects of the resent invention may be accomplished with a class of pyrazinoylguanidine compounds representing a compound represented by formula (I):

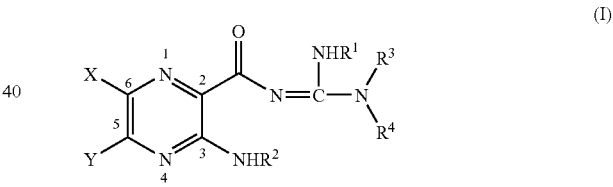

(I)

wherein

X is hydrogen, halogen, trifluoromethyl, lower alkyl, unsubstituted or substituted phenyl, lower alkyl-thio, phenyl-lower alkyl-thio, lower alkyl-sulfonyl, or phenyl-lower alkyl-sulfonyl;

Y is hydrogen, hydroxyl, mercapto, lower alkoxy, lower alkyl-thio, halogen, lower alkyl, unsubstituted or substituted mononuclear aryl, or $—N(R^2)_2$;

$R^1$ is hydrogen or lower alkyl;

each $R^2$ is, independently, $—R^7$, $—(CH_2)_m—OR^8$, $—(CH_2)_m—NR^7R^{10}$, $—(CH_2)_n(CHOR^8)(CHOR^8)_n—CH_2OR^8$, $—(CH_2CH_2O)_m—R^8$, $—(CH_2CH_2O)_m—CH_2CH_2NR^7R^{10}$, $—(CH_2)_n—C(=O)NR^7R^{10}$, $—(CH_2)_n—Z_g—R^7$, $—(CH_2)_m—NR^{10}—CH_2(CHOR^8)(CHOR^8)_n—CH_2OR^8$, $—(CH_2)_n—CO_2R^7$, or

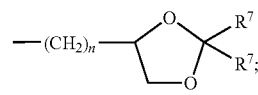

R³ and R⁴ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl; naphthyl-lower alkyl, or pyridyl-lower alkyl, with the proviso that at least one of R³ and R⁴ is a group represented by formula (A):

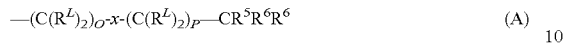  (A)

wherein each $R^L$ is, independently, —R⁷, —(CH₂)$_n$—OR⁸, —O—(CH₂)$_m$—OR⁸, —(CH₂)$_n$—NR⁷R¹⁰, —O—(CH₂)$_m$—NR⁷R¹⁰, —(CH₂)$_n$(CHOR⁸)(CHOR⁸)$_n$—CH₂OR⁸, —O—(CH₂)$_m$(CHOR⁸)(CHOR⁸)$_n$—CH₂OR⁸, —(CH₂CH₂O)$_m$—R⁸, —O—(CH₂CH₂O)$_m$—R⁸, —(CH₂CH₂O)$_m$—CH₂CH₂NR⁷R¹⁰, —O—(CH₂CH₂O)$_m$—CH₂CH₂NR⁷R¹⁰, —(CH₂)$_n$—C(=O)NR⁷R¹⁰, —O—(CH₂)$_m$—C(=O)NR⁷R¹⁰, —(CH₂)$_n$—(Z)$_g$—R⁷, —O—(CH₂)$_m$—(Z)$_g$—R⁷, —(CH₂)$_n$—NR¹⁰—CH₂(CHOR⁸)(CHOR⁸)$_n$—CH₂OR⁸, —O—(CH₂)$_m$—NR¹⁰—CH₂(CHOR⁸)(CHOR⁸)$_n$—CH₂OR⁸, —(CH₂)$_n$—CO₂R⁷, —O—(CH₂)$_m$—CO₂R⁷, —OSO₃H, —O-glucuronide, —O-glucose,

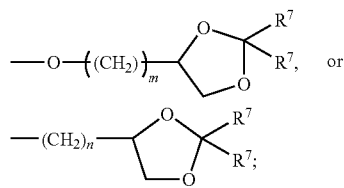

each o is, independently, an integer from 0 to 10;
each p is an integer from 0 to 10;
with the proviso that the sum of o and p in each contiguous chain is from 1 to 10;
each x is, independently, O, NR¹⁰, C(=O), CHOH, C(=N—R¹⁰), CHNR⁷R¹⁰, or represents a single bond;
wherein each R⁵ is, independently;
Link —(CH₂)$_n$—CR¹¹R¹¹—CAP, Link —(CH₂)$_n$(CHOR⁸)(CHOR⁸)$_n$—CR¹¹R¹¹—CAP, Link —(CH₂CH₂O)$_m$—CH₂—CR¹¹R¹¹—CAP, Link —(CH₂CH₂O)$_m$—CH₂CH₂—CR¹¹R¹¹—CAP, Link —(CH₂)$_n$(Z)$_g$—CR¹¹R¹¹—CAP, Link —(CH₂)$_n$(Z)$_g$—(CH₂)$_m$—CR¹¹R¹¹—CAP, Link —(CH₂)$_n$—NR¹³—CH₂(CHOR⁸)(CHOR⁸)$_n$—CR¹¹R¹¹—CAP, Link —(CH₂)$_n$—(CHOR⁸)$_m$CH₂—NR¹³—(Z)$_g$—CR¹¹R¹¹—CAP, Link —(CH₂)$_n$NR¹³—(CH₂)$_m$(CHOR⁸)$_n$CH₂NR¹³—(Z)$_g$—CR¹¹R¹¹—CAP, Link —(CH₂)$_m$—(Z)$_g$—(CH₂)$_m$—CR¹¹R¹¹—CAP, Link NH—C(=O)—NH—(CH₂)$_m$—CR¹¹R¹¹—CAP, Link —(CH₂)$_m$—C(=O)NR¹³—(CH₂)$_m$—CR¹¹R¹¹—CAP, Link —(CH₂)$_n$—(Z)$_g$—(CH₂)$_m$—(Z)$_g$—CR¹¹R¹¹—CAP, Link —Z$_g$—(CH₂)$_m$-Het-(CH₂)$_m$—CR¹¹R¹¹—CAP, wherein Link is, independently,
—O—, (CH₂)$_n$—, —O(CH₂)$_m$—, —NR¹³—C(=O)—NR¹³, —NR¹³—C(=O)—(CH₂)$_m$—, —C(=O) NR¹³—(CH₂)$_m$—, —(CH₂)$_n$—Z$_g$—(CH₂)$_n$—, —S—, —SO—, —SO₂—, SO₂NR⁷—, SO₂NR¹⁰—, -Het-.

wherein each CAP is, independently,

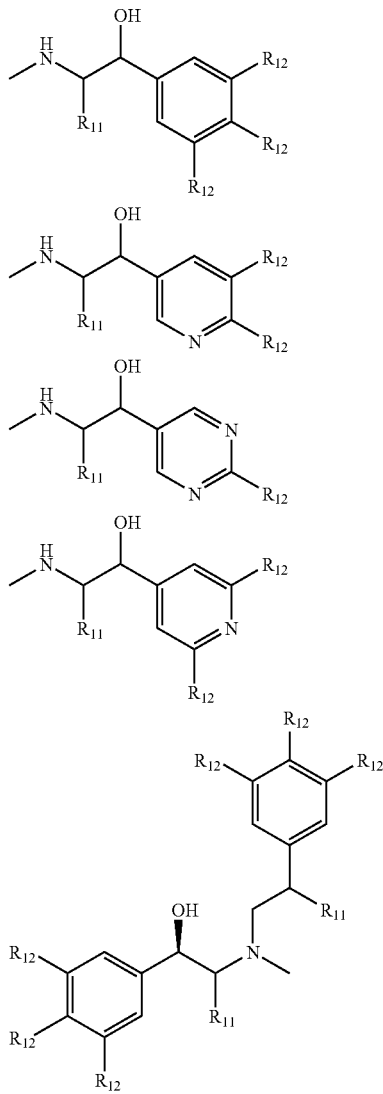

each R⁶ is, independently, —R⁷, —OR⁷, —OR¹¹, —N(R⁷)₂, —(CH₂)$_m$—OR⁸, —O—(CH₂)$_m$—OR⁸, —(CH₂)$_n$—NR⁷R¹⁰, —O—(CH₂)$_m$—NR⁷R¹⁰, —(CH₂)$_n$(CHOR⁸)(CHOR⁸)$_n$—CH₂OR⁸, —O—(CH₂)$_m$(CHOR⁸)(CHOR⁸)$_n$—CH₂OR⁸, —(CH₂CH₂O)$_m$—R⁸, —O—(CH₂CH₂O)$_m$—R⁸, —(CH₂CH₂O)$_m$—CH₂CH₂NR⁷R¹⁰, —O—(CH₂CH₂O)$_m$—CH₂CH₂NR⁷R¹⁰, —(CH₂)$_n$—C(=O)NR⁷R¹⁰, —O—(CH₂)$_m$—C(=O)NR⁷R¹⁰, —(CH₂)$_n$—(Z)$_g$—R⁷, —O—(CH₂)$_m$—(Z)$_g$—R⁷, —(CH₂)$_n$—NR¹⁰—CH₂(CHOR⁸)(CHOR⁸)$_n$—CH₂OR⁸, —O—(CH₂)$_m$—NR¹⁰—CH₂(CHOR⁸)(CHOR⁸)$_n$—CH₂OR⁸, —(CH₂)$_n$—CO₂R⁷, —O—(CH₂)$_m$—CO₂R⁷, —OSO₃H, —O-glucuronide, —O-glucose,

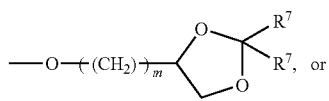

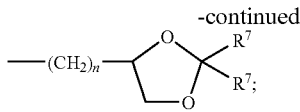

where when two $R^6$ are —$OR^{11}$ and are located adjacent to each other on a phenyl ring, the alkyl moieties of the two $R^6$ may be bonded together to form a methylenedioxy group; with the proviso that when at least two —$CH_2OR^8$ are located adjacent to each other, the $R^8$ groups may be joined to form a cyclic mono- or di-substituted 1,3-dioxane or 1,3-dioxolane, each $R^7$ is, independently, hydrogen lower alkyl, phenyl, or substituted phenyl;

each $R^8$ is, independently, hydrogen, lower alkyl, —C(=O)—$R^{11}$, glucuronide, 2-tetrahydropyranyl, or

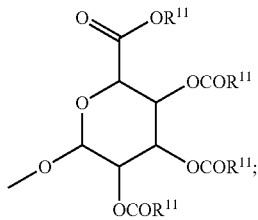

each $R^9$ is, independently, —$CO_2R^{13}$, —$CON(R^{13})_2$, —$SO_2CH_2R^{13}$, or —C(=O)$R^{13}$;

each $R^{10}$ is, independently, —H, —$SO_2CH_3$, —$CO_2R^7$, —C(=O)$NR^7R^9$, —C(=O)$R^7$, or —$(CH_2)_m$—$(CHOH)_n$—$CH_2OH$, each Z is, independently, CHOH, C(=O), —$(CH_2)_n$—, $CHNR^{13}R^{13}$, C=$NR^{13}$, or $NR^{13}$;

each $R^{11}$ is, independently, hydrogen, lower alkyl, phenyl lower alkyl or substituted phenyl lower alkyl;

each $R^{12}$ is independently, —$(CH_2)_n$—$SO_2CH_3$, —$(CH_2)_n$—$CO_2R^{13}$, —$(CH_2)_n$—, —C(=O)$NR^{13}R^{13}$, —$(CH_2)_n$—C(=O)$R^{13}$, —$(CH_2)_n$—(CHOH)$_n$—$CH_2OH$, —NH—$(CH_2)_n$—$SO_2CH_3$, —NH—$(CH_2)_n$—C(=O)$R^{11}$, —NH—C(=O)—NH—C(=O)$R^{11}$, —C(=O)$NR^{13}R^{13}$, —$OR^{11}$, —NH—$(CH_2)_n$—$R^{10}$, —Br, —Cl, —F, —I, $SO_2NHR^{11}$, —$NHR^{13}$, —NH—C(=O)—$NR^{13}R^{13}$, NH—$(CH_2)_n$—$SO_2CH_3$, NH—$(CH_2)_n$—C(=O)$R^{11}$, —NH—C(=O)—NH—C(=O)$R^{11}$, —C(=O)$NR^{13}R^{13}$, —$OR^{11}$, —$(CH_2)_n$—$NHR^{13}$, —NH—C(=O)—$NR^{13}R^{13}$, or —NH—$(CH_2)_n$—C(=O)—$R^{13}$;

each $R^{13}$ is, independently, hydrogen, lower alkyl, phenyl, substituted phenyl, —$SO_2CH_3$, —$CO_2R^7$, —C(=O)$NR^7R^7$, —C(=O)$NR^7SO_2CH_3$, —C(=O)$NR^7$—$CO_2R^7$, —C(=O)$NR^7$—C(=O)$NR^7R^7$, —C(=O)$NR^7$—C(=O)$R^7$, —C(=O)$NR^7$—$(CH_2)_m$—$(CHOH)_n$—$CH_2OH$, —C(=O)$R^7$, —$(CH_2)_m$—$(CHOH)_n$—$CH_2OH$, —$(CH_2)_m$—$NR^7R^{10}$, —$(CH_2)_m$—$NR^7R^7R^7$, —$(CH_2)_m$—$(CHOR^8)_m$—$(CH_2)_m$$NR^7R^7$, —$(CH_2)_M$—$NR^{10}R^{10}$, —$(CH_2)_m$—$(CHOR^8)_m$—$(CH_2)_m NR^7R^7R^7$,

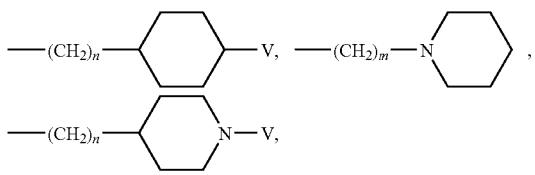

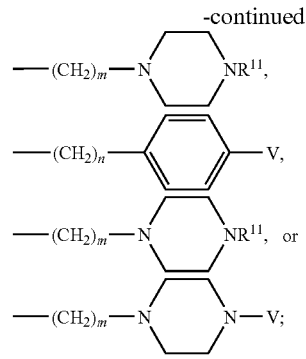

with the proviso that $NR^{13}R^{13}$ can be joined on itself to form a group represented by one of the following:

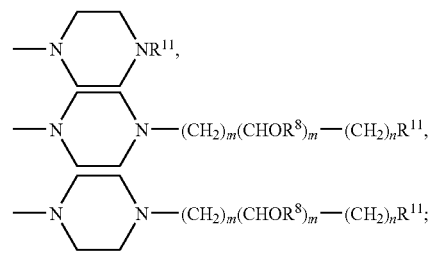

each Het is independently, —$NR^{13}$, —S—, —SO—, —$SO_2$—, —O—, —$SO_2NR^{13}$—, —$NHSO_2$—, —$NR^{13}CO$—, or —$CONR^{13}$—;

each g is, independently, an integer from 1 to 6;
each m is, independently, an integer from 1 to 7;
each n is, independently, an integer from 0 to 7;
each V is, independently, —$(CH_2)_m$—$NR^7R^{10}$, —$(CH_2)_m$—$NR^7R^7$, —$(CH_2)_m$—+$NR^{11}R^{11}R^{11}$, —$(CH_2)_n$—$(CHOR^8)_m$—$(CH_2)_m NR^7R^{10}$, —$(CH_2)_n$—$NR^{10}R^{10}$+—$(CH_2)_n$—$(CHOR^8)_m$—$(CH_2)_m NR^7R^7$, —$(CH_2)_n$—$(CHOR^8)_m$—$(CH_2)_m NR^{11}R^{11}R^{11}$ with the proviso that when V is attached directly to a nitrogen atom, then V can also be, independently, $R^7$, $R^{10}$, or $(R^{11})_2$;

wherein for of the above compounds when two —$CH_2OR^8$ groups are located 1,2- or 1,3- with respect to each other the $R^8$ groups may be joined to form a cyclic mono- or di-substituted 1,3-dioxane or 1,3-dioxolane;

wherein any of the above compounds can be a pharmaceutically acceptable salt thereof, and wherein the above compounds are inclusive of all racemates, enantiomers, diastereomers, tautomers, polymorphs and pseudopolymorphs thereof.

The present invention also provides pharmaceutical compositions which contain a compound described above.

The present invention also provides a method of promoting hydration of mucosal surfaces, comprising:
administering an effective amount of a compound represented by formula (I) to a mucosal surface of a subject.

The present invention also provides a method of restoring mucosal defense, comprising:
topically administering an effective amount of compound represented by formula (I) to a mucosal surface of a subject in need thereof.

The present invention also provides a method of blocking ENaC, comprising:

contacting sodium channels with an effective amount of a compound represented by formula (I).

The present invention also provides a method of promoting mucus clearance in mucosal surfaces, comprising:

administering an effective amount of a compound represented by formula (I) to a mucosal surface of a subject.

The present invention also provides a method of treating chronic bronchitis, comprising:

administering an effective amount of a compound represented by formula (I) to a subject in need thereof.

The present invention also provides a method of treating cystic fibrosis, comprising:

administering an effective amount of compound represented by formula (I) to a subject in need thereof.

The present invention also provides a method of treating rhinosinusitis, comprising:

administering an effective amount of a compound represented by a formula (I) to a subject in need thereof.

The present invention also provides a method of treating nasal dehydration, comprising:

administering an effective amount of a compound represented by formula (I) to the nasal passages of a subject in need thereof.

In a specific embodiment, the nasal dehydration is brought on by administering dry oxygen to the subject.

The present invention also provides a method of treating sinusitis, comprising:

administering an effective amount of a compound represented by formula (I) to a subject in need thereof.

The present invention also provides a method of treating pneumonia, comprising:

administering an effective amount of a compound represented by formula (I) to a subject in need thereof.

The present invention also provides a method of preventing ventilator-induced pneumonia, comprising:

administering an effective compound represented by formula (I) to a subject by means of a ventilator.

The present invention also provides a method of treating asthma, comprising:

administering an effective amount of a compound represented by formula (I) to a subject in need thereof.

The present invention also provides a method of treating primary ciliary dyskinesia, comprising:

administering an effective amount of a compound represented by formula (I) to a subject in need thereof.

The present invention also provides a method of treating otitis media, comprising:

administering an effective amount of a compound represented by formula (I) to a subject in need thereof.

The present invention also provides a method of inducing sputum for diagnostic purposes, comprising:

administering an effective amount of compound represented by formula (I) to a subject in need thereof.

The present invention also provides a method of treating chronic obstructive pulmonary disease, comprising:

administering an effective amount of a compound represented by formula (I) to a subject in need thereof.

The present invention also provides a method of treating emphysema, comprising:

administering an effective amount of a compound represented by formula (I) to a subject in need thereof.

The present invention also provides a method of treating dry eye, comprising:

administering an effective amount of a compound represented by formula (I) to the eye of the subject in need thereof.

The present invention also provides a method of promoting ocular hydration, comprising:

administering an effective amount of a compound represented by formula (I) to the eye of the subject.

The present invention also provides a method of promoting corneal hydration, comprising:

administering an effective amount of a compound represented by formula (I) to the eye of the subject.

The present invention also provides a method of treating Sjögren's disease, comprising:

administering an effective amount of compound represented by formula (I) to a subject in need thereof.

The present invention also provides a method of treating vaginal dryness, comprising:

administering an effective amount of a compound represented by formula (I) to the vaginal tract of a subject in need thereof.

The present invention also provides a method of treating dry skin, comprising:

administering an effective amount of a compound represented by formula (I) to the skin of a subject in need thereof.

The present invention also provides a method of treating dry mouth (xerostomia), comprising:

administering an effective amount of compound represented by formula (I) to the mouth of the subject in need thereof.

The present invention also provides a method of treating distal intestinal obstruction syndrome, comprising:

administering an effective amount of compound represented by formula (I) to a subject in need thereof.

The present invention also provides a method of treating esophagitis, comprising:

administering an effective amount of a compound represented by formula (I) to a subject in need thereof.

The present invention also provides a method of treating constipation, comprising:

administering an effective amount of a compound represented by formula (I) to a subject in need thereof. In one embodiment of this method, the compound is administered either orally or via a suppository or enema.

The present invention also provides a method of treating chronic diverticulitis comprising:

administering an effective amount of a compound represented by formula (I) to a subject in need thereof.

BRIEF DESCRIPTION OF THE FIGURES

FIG. 4 shows the tautomers of the compounds of formula I.

DETAILED DESCRIPTION OF THE INVENTION

Figure 1:
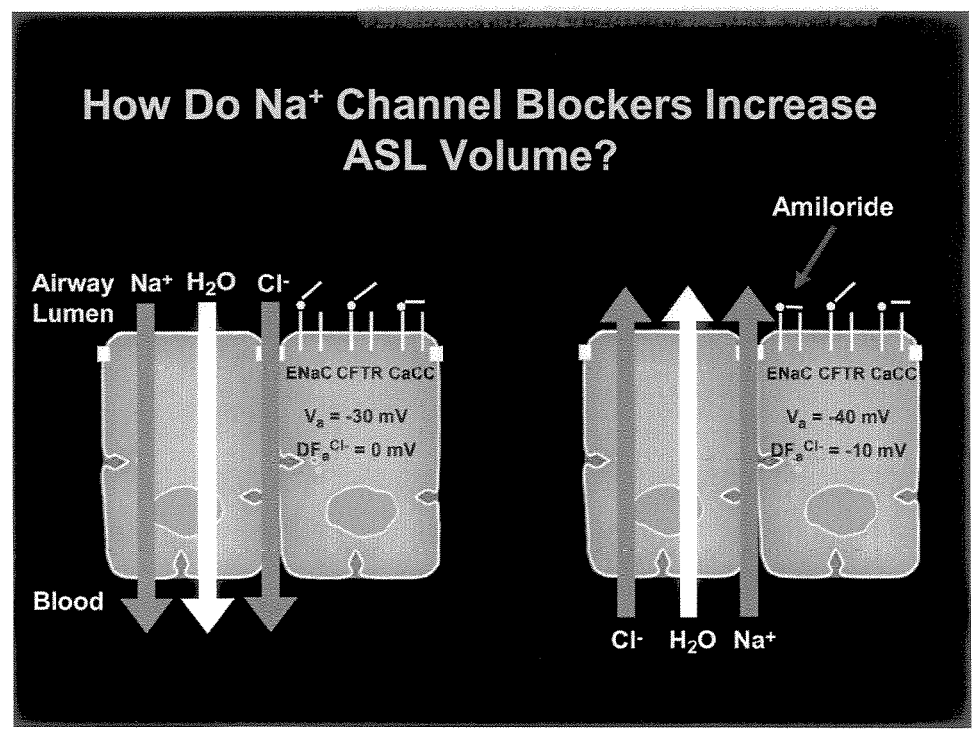
FIG. 1 shows the baseline activity of sodium channels before and after blockade with amiloride.

The present invention is based on the discovery that the compounds of formula (I) also possess both sodium channel blocking activity and beta agonist activity in the same molecule.

The present invention is also based on the discovery that the compounds of formula (I) are more potent and/or, absorbed less rapidly from mucosal surfaces, especially airway surfaces, and/or less reversible from interactions with ENaC as compared to compounds such as amiloride, benzamil, and phenamil. Therefore, the compounds of formula (I) have a longer half-life on mucosal surfaces as compared to these compounds.

The present invention is also based on the discovery that certain compounds embraced by formula (I) are converted in vivo into metabolic derivatives thereof that have reduced efficacy in blocking sodium channels and acting as beta-adrenergic receptor agonists as compared to the parent administered compound, after they are absorbed from mucosal surfaces after administration. This important property means that the compounds will have a lower tendency to cause undesired side-effects by blocking sodium channels and activating beta-receptors located at other untargeted locations in the body of the recipient, e.g., in the kidneys and heart.

Mono drug therapy leaves most major diseases such as chronic bronchitis and cystic fibrosis inadequately treated. It is therefore often necessary to discover and develop novel drugs or combination of drugs which treat and modulate multiple targets simultaneously (polypharmacology) with the goal of enhancing efficacy or improving safety relative to single target drugs. There are three possible ways to achieve this, 1) Combining therapeutic "cocktails" of two or more individual drugs; the benefits of this approach are often lessened by poor patient compliance. 2). A multiple component drug ("fixed combination" or multiple component drug) that contains two or more agents in a single tablet, liquid formulation, inhaler or dry powder device. This can sometimes improve patient compliance versus multiple component drugs but adds the complexity of carefully dosing so as to minimize multiple metabolic pathways. 3). A single molecular entity which can simultaneously modulate multiple drug targets (designed multiple ligands). The advantage of a multiple ligand over the first two approaches is that it improves compliance, enhances efficacy, it targets a known set of deficiencies in multiple systems with a single new chemical entity, it often lacks the unpredictable differences in the pharmacokinetic and pharmacodynamic variability between patients, it is often easier to formulate and potentially lowers the risk of drug-drug interactions compared to drug cocktails and multiple component drugs. It was therefore our goal to discover multiple ligands that have both sodium channel blocking activity as well as beta agonist activity.

The addition of beta-adrenergic receptor agonist activity to a sodium channel blocker will significantly increase the capacity to hydrate airway surfaces in subjects in need of hydration for therapeutic purposes. The mechanism by which beta-agonist activity adds to the hydration capacity of Na channel blockers alone, or beta-agonists alone, is described in the following diagrams that describe the electrochemical gradients for ion flows and the net secretion that results from these forces in airway epithelia.

As shown in FIG. 1, under baseline conditions human airway epithelia absorb NaCl and $H_2O$. Active $Na^+$ absorption drives this process. $Cl^-$ is absorbed passively with $Na^+$ to preserve electroneutrality. As there is no net driving force for $Cl^-$ to move across the apical cell membrane, $Cl^-$ is absorbed paracellularly in response to the transepithelial electric potential. Water moves cellularly and paracellularly in response to the osmotic gradients generated by NaCl absorbtion.

Application of a $Na^+$ channel blocker (as an example amiloride is shown) inhibits the entry of $Na^+$ into the cell which: (1) abolishes $Na^+$ absorption and (2) hyperpolarizes the apical cell membrane (Va). The hyperpolarization of Va generates an electrochemical driving force favoring $Cl^-$ secretion ($Na^+$ now follows in the secretory direction via the paracellular path). The rate of $Cl^-$ secretion is proportional to the activity of the apical membrane $Cl^-$ channels which are typically 30-50% maximally active under basal conditions. In summary, application of a $Na^+$ channel blocker inhibits $Na^+$ absorption and triggers a modest amount of $Cl^-$ secretion. Note again that water will follow transcellularly in response to the secreted NaCl.

Figure 2:
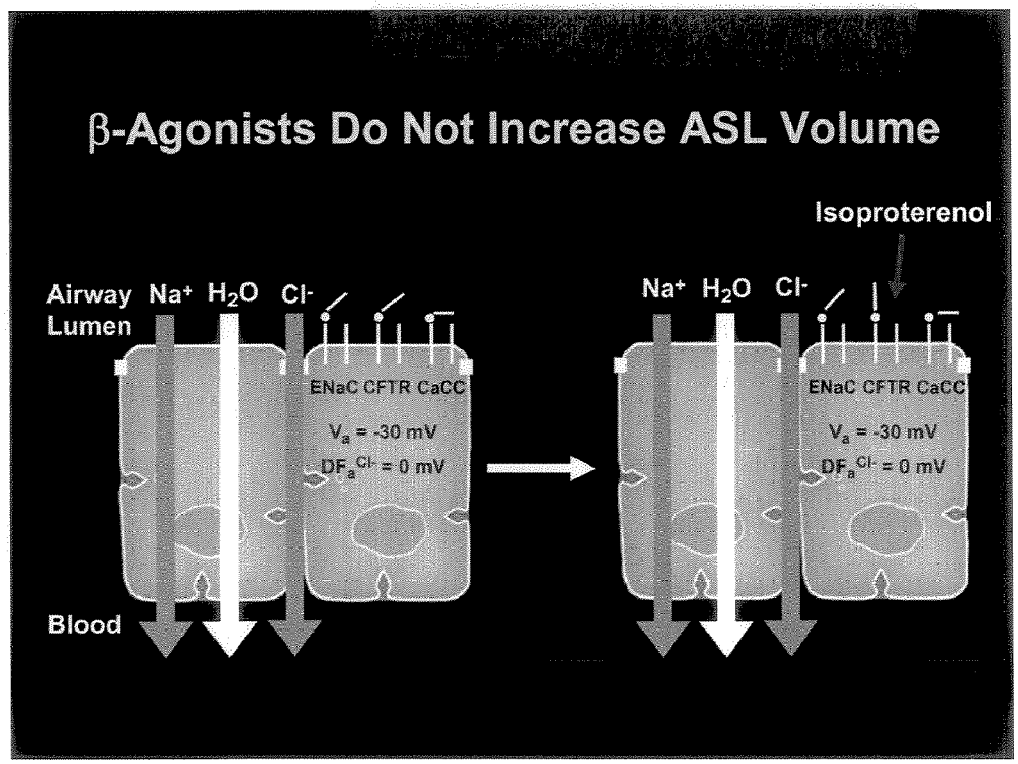
FIG. 2 shows the activity of sodium channels before and after the addition of a beta-agonist.

In contrast, as depicted in FIG. 2, addition of a beta-agonist (as an example isoproterenol is shown) alone to human airway epithelia produces no changes in $Na^+$ absorption or $Cl^-$ secretion. The reason for this absence of effect is that there is no electrochemical driving force for $Cl^-$ to move across the cell (See the following references: Intracellular $Cl^-$ activity and cellular $Cl^-$ pathways in cultured human airway epithelium. Am J Physiol. 1989 May; 256(5 Pt 1):C1033-44. Willumsen N J, Davis C W, Boucher R C Cellular $Cl^-$ transport in cultured cystic fibrosis airway epithelium. Am J Physiol. 1989 May; 256(5 Pt 1):C1045-53. Willumsen N J, Davis C W, Boucher R C Activation of an apical $Cl^-$ conductance by Ca2+ ionophores in cystic fibrosis airway epithelia. Am J Physiol. 1989 February; 256(2 Pt 1):C226-33. Willumsen N J, Boucher R C). Thus, a beta-agonist mediated activation of an apical membrane $Cl^-$ channel, usually CFTR via changes in cAMP, produces no change in the rate of movement of $Cl^-$ across the barrier and, hence, no change in transepithelial sodium chloride or water secretion.

Figure 3:
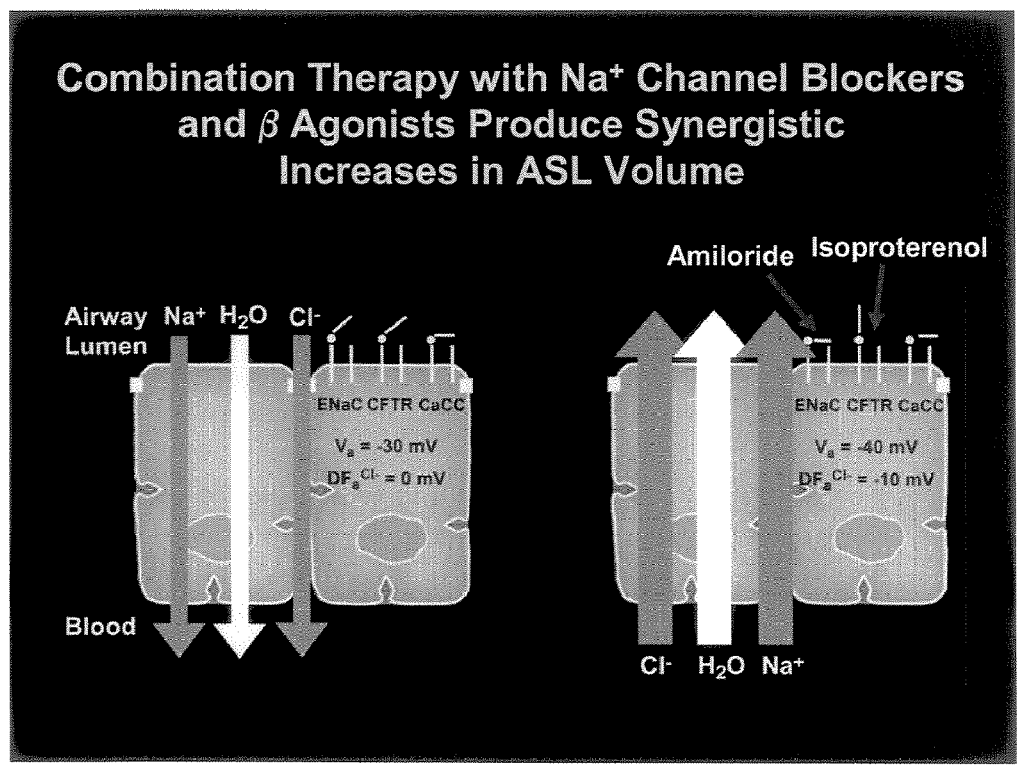
FIG. 3 shows the mechanism underlying the additivity of a Na channel blocker and a beta-agonist.

However, when a Na channel blocker is administered with a beta-agonist, additivity between these two classes of compounds is achieved with the result being accelerated $Cl^-$ (and $Na^+$, $H_2O$) secretion. The mechanism underlying the additivity is shown in FIG. 3. In the presence of a Na channel blocker, an electrochemical gradient for $Cl^-$ secretion is generated (also see FIG. 1). Now when a beta-agonist is present, it converts the apical membrane CFTR from ~30% basal activity to ~100% activity via beta-agonist induced increase in cAMP that ultimately activates CFTR via PKA (protein kinase A). Because there is an electrochemical driving force favoring $Cl^-$ secretion as a result of ENaC blockade, the increase in $Cl^-$ channel activity translates into increasing $Cl^-$ (and $Na^+$, $H_2O$) secretion. Thus, the hydration capacity of the epithelia is greatly enhanced by the presence of both $Na^+$ channel blocker and beta-adrenergic receptor agonist activities in the environment bathing the human airway epithelia as compared to just $Na^+$ channel blocker or beta-adrenergic receptor agonist by themselves. A discovery of this invention is that administration of both activities contained within the same molecule to the epithelium is at least as effective as sequential administration of a Na channel blocker followed by a beta-agonist and therefore has the advantages cited earlier.

The compounds of formula I exist primarily as a combination of the three tautomers shown in FIG. 4. The compounds of formula I exist primarily as a combination of the three tautomers shown in FIG. 4. FIG. 4 shows the three tautomers represented in formula I that exist in solution. Previous studies (R L Smith et. Al. Journal of the American Chemical Society, 1979, 101, 191-201) have shown that the free base exists primarily as the acylimino tautomer, whereas the physiologically active species exists as the protonated form of the acylamino. These structural representations have been used to represent amiloride and its analogs in both the patent and scientific literature. We use both the acylamino and acylimino representations for convenience throughout this patent with the understanding that the structures are in reality a hybrid of the three forms with the actual amount of each dependent on the pH, the one of action and the nature of the substituents.

In the compounds represented by formula (I), X may be hydrogen, halogen, trifluoromethyl, lower alkyl, lower cycloalkyl, unsubstituted or substituted phenyl, lower alkyl-thio, phenyl-lower alkyl-thio, lower alkyl-sulfonyl, or phenyl-lower alkyl-sulfonyl. Halogen is preferred.

Examples of halogen include fluorine, chlorine, bromine, and iodine. Chlorine and bromine are the preferred halogens. Chlorine is particularly preferred. This description is applicable to the term "halogen" as used throughout the present disclosure.

As used herein, the term "lower alkyl" means an alkyl group having less than 8 carbon atoms. This range includes all specific values of carbon atoms and subranges there between, such as 1, 2, 3, 4, 5, 6, and 7 carbon atoms. The term "alkyl" embraces all types of such groups, e.g., linear, branched, and cyclic alkyl groups. This description is applicable to the term "lower alkyl" as used throughout the present disclosure. Examples of suitable lower alkyl groups include methyl, ethyl, propyl, cyclopropyl, butyl, isobutyl, etc.

Substituents for the phenyl group include halogens. Particularly preferred halogen substituents are chlorine and bromine.

Y may be hydrogen, hydroxyl, mercapto, lower alkoxy, lower alkyl-thio, halogen, lower alkyl, lower cycloalkyl, mononuclear aryl, or —N($R^2$)$_2$. The alkyl moiety of the lower alkoxy groups is the same as described above. Examples of mononuclear aryl include phenyl groups. The phenyl group may be unsubstituted or substituted as described above. The preferred identity of Y is —N($R^2$)$_2$. Particularly preferred are such compounds where each $R^2$ is hydrogen.

$R^1$ may be hydrogen or lower alkyl. Hydrogen is preferred for $R^1$.

Each $R^2$ may be, independently, —$R^7$, —(CH$_2$)$_m$—OR$^8$, —(CH$_2$)$_m$—NR$^7$R$^{10}$, —(CH$_2$)$_n$(CHOR$^8$)(CHOR$^8$)$_n$—CH$_2$OR$^8$, —(CH$_2$CH$_2$O)$_m$—R$^8$, —(CH$_2$CH$_2$O)$_m$—CH$_2$CH$_2$NR$^7$R$^{10}$, —(CH$_2$)$_n$—C(=O)NR$^7$R$^{10}$, —(CH$_2$)$_n$—Z$_g$—R$^7$, —(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, or

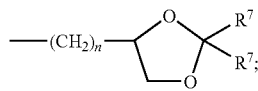

Hydrogen and lower alkyl, particularly $C_1$-$C_3$ alkyl are preferred for $R^2$. Hydrogen is particularly preferred.

$R^3$ and $R^4$ may be, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, provided that at least one of $R^3$ and $R^4$ is a group represented by formula (A).

Preferred compounds are those where one of $R^3$ and $R^4$ is hydrogen and the other is represented by formula (A).

In formula (A), the moiety —(C($R^L$)$_2$)$_o$-x-(C($R^L$)$_2$)$_p$— defines an alkylene group. The variables o and p may each be an integer from 0 to 10, subject to the proviso that the sum of o and p in the chain is from 1 to 10. Thus, o and p may each be 0, 1, 2, 3, 4, 5, 6, 7, 8, 9, or 10. Preferably, the sum of o and p is from 2 to 6. In a particularly preferred embodiment, the sum of o and p is 4.

The linking group in the alkylene chain, x, may be, independently, O, NR$^{10}$, C(=O), CHOH, C(=N—R$^{10}$), CHNR$^7$R$^{10}$, or represents a single bond;

Therefore, when x represents a single bond, the alkylene chain bonded to the ring is represented by the formula —(C($R^L$)$_2$)$_{o+p}$—, in which the sum o+p is from 1 to 10.

Each $R^L$ may be, independently, —$R^7$, —(CH$_2$)$_n$—OR$^8$, —O—(CH$_2$)$_m$—OR$^8$, —(CH$_2$)$_n$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$)$_n$—C(=O)NR$^7$R$^{10}$, —O—(CH$_2$)$_m$—C(=O)NR$^7$R$^{10}$, —(CH$_2$)$_n$—(Z)$_g$—R$^7$, —O—(CH$_2$)$_m$—(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$, —OSO$_3$H, —O-glucuronide, —O-glucose,

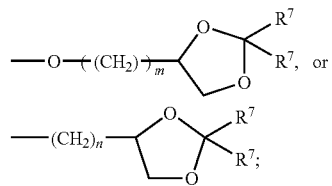

The preferred $R^L$ groups include —H, —OH, —N($R^7$)$_2$, especially where each $R^7$ is hydrogen.

In the alkylene chain in formula (A), it is preferred that when one $R^L$ group bonded to a carbon atoms is other than hydrogen, then the other $R^L$ bonded to that carbon atom is hydrogen, i.e., the formula —CHR$^L$—. It is also preferred that at most two $R^L$ groups in an alkylene chain are other than hydrogen, where in the other $R^L$ groups in the chain are hydrogens. Even more preferably, only one $R^L$ group in an alkylene chain is other than hydrogen, where in the other $R^L$ groups in the chain are hydrogens. In these embodiments, it is preferable that x represents a single bond.

In another particular embodiment of the invention, all of the $R^L$ groups in the alkylene chain are hydrogen. In these embodiments, the alkylene chain is represented by the formula —(CH$_2$)$_o$-x-(CH$_2$)$_p$—.

Each $R^5$ is, independently,

Link —(CH$_2$)$_n$—CR$^{11}$R$^{11}$—CAP, Link —(CH$_2$)$_n$(CHOR$^8$)(CHOR$^8$)$_n$—CR$^{11}$R$^{11}$—CAP, Link —(CH$_2$CH$_2$O)$_m$—CH$_2$—CR$^{11}$R$^{11}$—CAP, Link —(CH$_2$CH$_2$O)$_m$—CH$_2$CH$_2$—CR$^{11}$R$^{11}$—CAP, Link —(CH$_2$)$_n$—(Z)$_g$—CR$^{11}$R$^{11}$—CAP, Link —(CH$_2$)$_n$(Z)$_g$—(CH$_2$)$_m$—CR$^{11}$R$^{11}$—CAP, Link —(CH$_2$)$_n$—NR$^{13}$—CH$_2$(CHOR$^8$)(CHOR$^8$)$_n$—CR$^{11}$R$^{11}$—CAP, Link —(CH$_2$)$_n$—(CHOR$^8$)$_m$CH$_2$—NR$^{13}$—(Z)$_g$—CR$^{11}$R$^{11}$—CAP, Link —(CH$_2$)$_n$NR$^{13}$—(CH$_2$)$_m$(CHOR$^8$)$_n$CH$_2$NR$^{13}$—(Z)$_g$—CR$^{11}$R$^{11}$—CAP, Link —(CH$_2$)$_m$—(Z)$_g$—(CH$_2$)$_m$—CR$^{11}$R$^{11}$—CAP, Link NH—C(=O)—NH—(CH$_2$)$_m$—CR$^{11}$R$^{11}$—CAP, Link —(CH$_2$)$_m$—C(=O)NR$^{13}$—(CH$_2$)$_m$—CR$^{11}$R$^{11}$—CAP, Link —(CH$_2$)$_n$—(Z)$_g$—(CH$_2$)$_m$—(Z)$_g$—CR$^{11}$R$^{11}$—CAP, or Link —Z$_g$—(CH$_2$)$_m$-Het-(CH$_2$)$_m$—CR$^{11}$R$^{11}$—CAP.

Each Link is, independently,

—O—, (CH$_2$)$_n$—, —O(CH$_2$)$_m$—, —NR$^{13}$—C(=O)—NR$^{13}$, —NR$^{13}$—C(=O)—(CH$_2$)$_m$—, —C(=O)NR$^{13}$—(CH$_2$)$_m$, —(CH$_2$)$_n$—Z$_g$—(CH$_2$)$_n$, —S—, —SO—, —SO$_2$—, SO$_2$NR$^7$—, SO$_7$NR$^{10}$—, -Het-.

Each CAP is, independently,

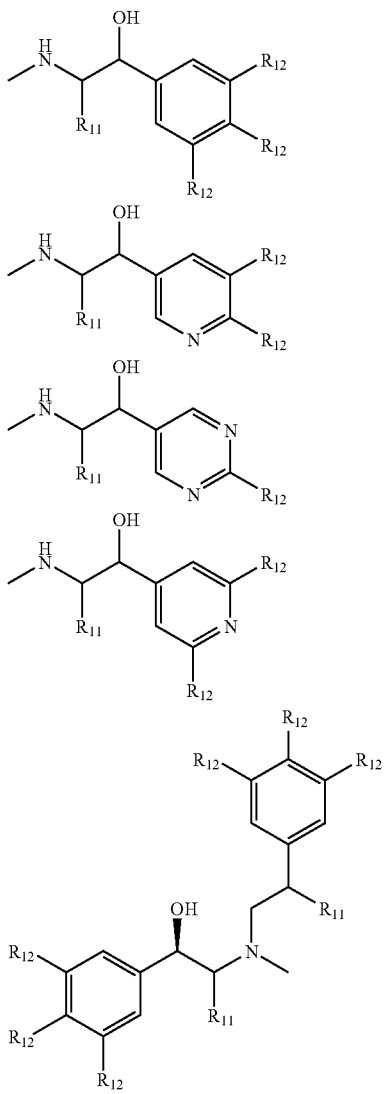

Each $R^6$ is, independently, $-R^7$, $-OR^7$, $-OR^{11}$, $-N(R^7)_2$, $-(CH_2)_m-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

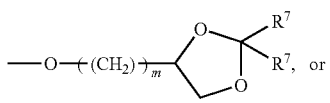

-continued

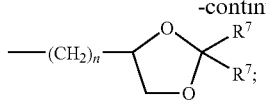

Each $R^7$ is, independently, hydrogen lower alkyl, phenyl, or substituted phenyl.

Each $R^8$ is, independently, hydrogen, lower alkyl, $-C(=O)-R^{11}$, glucuronide, 2-tetrahydropyranyl, or

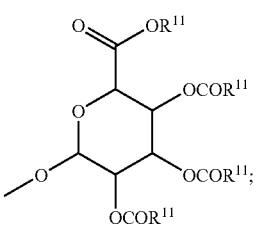

Each $R^9$ is, independently, $-CO_2R^{13}$, $-CON(R^{13})_2$, $-SO_2CH_2R^{13}$, or $-C(=O)R^{13}$, Each $R^{10}$ is, independently, $-H$, $-SO_2CH_3$, $-CO_2R^7$, $-C(=O)NR^7R^9$, $-C(=O)R^7$, or $-(CH_2)_m-(CHOH)_n-CH_2OH$.

Each Z is, independently, CHOH, C(=O), $-(CH_2)_n-$, $CHNR^{13}R^{13}$, $C=NR^{13}$, or $NR^{13}$.

Each $R^{11}$ is, independently, hydrogen, lower alkyl, phenyl lower alkyl or substituted phenyl lower alkyl.

Each $R^{12}$ is independently, $-(CH_2)_n-SO_2CH_3$, $-(CH_2)_n-CO_2R^{13}$, $-(CH_2)_n-C(=O)NR^{13}R^{13}$, $-(CH_2)_n-C(=O)R^{13}$, $-(CH_2)_n-(CHOH)_n-CH_2OH$, $-NH-(CH_2)_n-SO_2CH_3$, $NH-(CH_2)_n-C(=O)R^{11}$, $NH-C(=O)-NH-C(=O)R^{11}$, $-C(=O)NR^{13}R^{13}$, $-OR^{11}$, $-NH-(CH_2)_nR^{10}$, $-Br$, $-Cl$, $-F$, $-I$, $SO_2NHR^{11}$, $-NHR^{13}$, $-NH-C(=O)-NR^{13}R^{13}$, $NH-(CH_2)_n-SO_2CH_3$, $NH-(CH_2)_n-C(=O)R^{11}$, $-NH-C(=O)-NH-C(=O)R^{11}$, $-C(=O)NR^{13}R^{13}$, $-OR^{11}$, $-(CH_2)_n-NHR^{13}$, $-NH-C(=O)-NR^{13}R^{13}$, or $-NH-(CH_2)_n-C(=O)-R^{13}$;

Each $R^{13}$ is, independently, hydrogen, lower alkyl, phenyl, substituted phenyl, $-SO_2CH_3$, $-CO_2R^7$, $-C(=O)NR^7R^7$, $-C(=O)NR^7SO_2CH_3$, $-C(=O)NR^7-CO_2R^7$, $-C(=O)NR^7-C(=O)NR^7R^7$, $-C(=O)NR^7-C(=O)R^7$, $-C(=O)NR^7-(CH_2)_m-(CHOH)_n-CH_2OH$, $-C(=O)R^7$, $-(CH_2)_m-(CHOH)_n-CH_2OH$, $-(CH_2)_m-NR^7R^{10}$, $+-(CH_2)_m-NR^7R^7R^7$, $-(CH_2)_m-(CHOR^8)_m-(CH_2)_m$ $NR^7R^7$, $-(CH_2)_m-NR^{10}R^{10}$, $+-(CH_2)_m-(CHOR^8)_m-(CH_2)_mNR^7R^7R^7$,

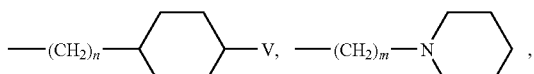

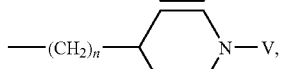

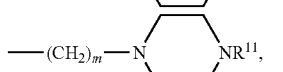

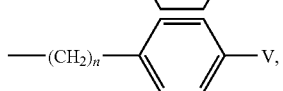

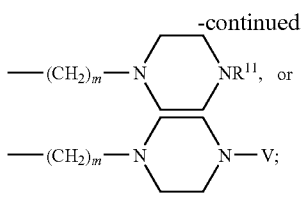

with the proviso that NR$^{13}$R$^{13}$ can be joined on itself to form a group represented by one of the following:

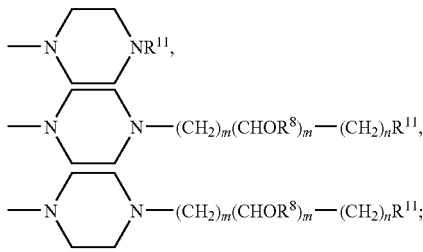

Each Het is independently, —NR$^{13}$, —S—, —SO—, —SO$_2$—; —O—, —SO$_2$NR$^{13}$—, —NHSO$_2$—, —NR$^{13}$CO—, —CONR$^{13}$—.

Each g is, independently, an integer from 1 to 6.
Each m is, independently, an integer from 1 to 7.
Each n is, independently, an integer from 0 to 7.
Each V is, independently, —(CH$_2$)$_m$—NR$^7$R$^{10}$, —(CH$_2$)$_m$—NR$^7$R$^7$, —(CH$_2$)$_m$—+NR$^{11}$R$^{11}$R$^{11}$, —(CH$_2$)$_n$—(CHOR$^8$)$_m$ —(CH$_2$)$_m$NR$^7$R$^{10}$, —(CH$_2$)$_n$—NR$^{10}$R$^{10}$+—(CH$_2$)$_n$—(CHOR$^8$)$_m$—(CH$_2$)$_m$NR$^7$R$^7$, —(CH$_2$)$_n$—(CHOR$^8$)$_m$—(CH$_2$)$_m$NR$^{11}$R$^{11}$R$^{11}$ with the proviso that when V is attached directly to a nitrogen atom, then V can also be, independently, R$^7$, R$^{10}$, or (R$^{11}$)$_2$.

In any of the compounds of the present invention, when two —CH$_2$OR$^8$ groups are located 1,2- or 1,3- with respect to each other the R$^8$ groups may be joined to form a cyclic mono- or di-substituted 1,3-dioxane or 1,3-dioxolane.

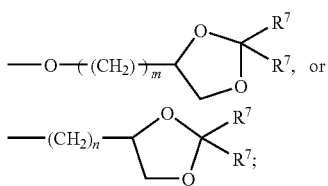

In another embodiment, when two R$^6$ are —OR$^{11}$ and are located adjacent to each other on a phenyl ring, the alkyl moieties of the two R$^6$ may be bonded together to form a methylenedioxy group.

In still another embodiment of the invention, when at least two —CH$_2$OR$^8$ are located adjacent to each other, the R$^8$ groups may be joined to form a cyclic mono- or di-substituted 1,3-dioxane or 1,3-dioxolane.

In addition, one of more of the R$^6$ groups can be one of the R$^5$ groups which fall within the broad definition of R$^6$ set forth above.

As discussed above, R$^6$ may be hydrogen. Therefore, 1, 2, 3, or 4 R$^6$ groups may be other than hydrogen. Preferably at most 3 of the R$^6$ groups are other than hydrogen.

Each g is, independently, an integer from 1 to 6. Therefore, each g may be 1, 2, 3, 4, 5, or 6.

Each m is an integer from 1 to 7. Therefore, each m may be 1, 2, 3, 4, 5, 6, or 7.

Each n is an integer from 0 to 7. Therefore, each n may be 0, 1, 2, 3, 4, 5, 6, or 7.

More specific examples of suitable groups represented by formula (A) are shown in formula below:

$$—(C(R^L)_2)_O-x-(C(R^L)_2)_P—CR^5R^6R^6 \qquad (A)$$

in which each RL is hydrogen and where o, x, p, R$^5$, and R$^6$, are as defined above.

In a preferred embodiment of the invention, Y is —NH$_2$.
In another preferred embodiment, R$^2$ is hydrogen.
In another preferred embodiment, R$^1$ is hydrogen.
In another preferred embodiment, X is chlorine.
In another preferred embodiment, R$^3$ is hydrogen.
In another preferred embodiment, R$^L$ is hydrogen.
In another preferred embodiment, o is 4.
In another preferred embodiment, p is 0.
In another preferred embodiment, the sum of o and p is 4.
In another preferred embodiment, x represents a single bond.
In another preferred embodiment, R$^6$ is hydrogen.
In another preferred embodiment, at most one Q is a nitrogen atom.
In another preferred embodiment, no Q is a nitrogen atom.
In a preferred embodiment of the present invention:
X is halogen;
Y is —N(R$^7$)$_2$;
R$^1$ is hydrogen or C$_1$-C$_3$ alkyl;
R$^2$ is —R$^7$, —OR$^7$, CH$_2$OR$^7$, or —CO$_2$R$^7$;
R$^3$ is a group represented by formula (A); and
R$^4$ is hydrogen, a group represented by formula (A), or lower alkyl;
In another preferred embodiment of the present invention:
X is chloro or bromo;
Y is —N(R$^7$)$_2$;
R$^2$ is hydrogen or C$_1$-C$_3$ alkyl;
at most three R$^6$ are other than hydrogen as described above;
at most three R$^L$ are other than hydrogen as described above
In another preferred embodiment of the present invention:
Y is —NH$_2$;
In another preferred embodiment of the present invention:
R$^4$ is hydrogen;
at most one R$^L$ is other than hydrogen as described above; and
at most two R$^6$ are other than hydrogen as described above.
In addition, one of more of the R$^6$ groups can be one of the R$^5$ groups which fall within the broad definition of R$^6$ set forth above.

As discussed above, R$^6$ may be hydrogen. Therefore, 1 or 2 R$^6$ groups may be other than hydrogen. Preferably at most 3 of the R$^6$ groups are other than hydrogen.

Each g is, independently, an integer from 1 to 6. Therefore, each g may be 1, 2, 3, 4, 5, or 6.

Each m is an integer from 1 to 7. Therefore, each m may be 1, 2, 3, 4, 5, 6, or 7.

Each n is an integer from 0 to 7. Therefore, each n maybe 0, 1, 2, 3, 4, 5, 6, or 7.

In a preferred embodiment of the invention, Y is —NH$_2$.
In another preferred embodiment, R$^2$ is hydrogen.
In another preferred embodiment, R$^1$ is hydrogen.
In another preferred embodiment, X is chlorine.
In another preferred embodiment, R$^3$ is hydrogen.
In another preferred embodiment, R$^L$ is hydrogen.
In another preferred embodiment, o is 4.

In another preferred embodiment, p is 2.
In another preferred embodiment, the sum of o and p is 6.
In another preferred embodiment, x represents a single bond.
In another preferred embodiment, $R^6$ is hydrogen.
In a preferred embodiment of the present invention:
X is halogen;
Y is —$N(R^7)_2$;
$R^1$ is hydrogen or $C_1$-$C_3$ alkyl;
$R^2$ is —$R^7$, —$OR^7$, $CH_2O^7$, or —$CO_2R^7$;
$R^3$ is a group represented by formula (A); and
$R^4$ is hydrogen, a group represented by formula (A), or lower alkyl;
In another preferred embodiment of the present invention:
X is chloro or bromo;
Y is —$N(R^7)_2$,
$R^2$ is hydrogen or $C_1$-$C_3$ alkyl;
at most three $R^6$ are other than hydrogen as described above; and
at most three $R^L$ are other than hydrogen as described above;

In another preferred embodiment of the present invention:
Y is —$NH_2$;
$R^4$ is hydrogen;
at most one $R^L$ is other than hydrogen as described above; and
at most two $R^6$ are other than hydrogen as described above;
In another preferred embodiment of the present invention the compound of formula (1) is represented by the formula:

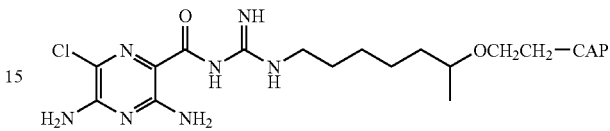

In another preferred embodiment of the present invention the compound of formula (1) is represented by the formula:

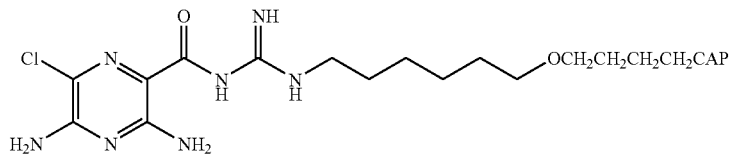

In another preferred embodiment of the present invention the compound of formula (1) is represented by the formula:

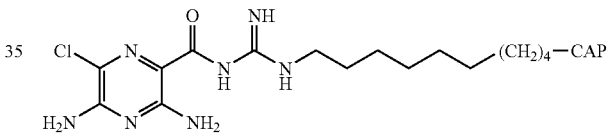

In another preferred embodiment of the present invention the compound of formula (1) is represented by the formula:

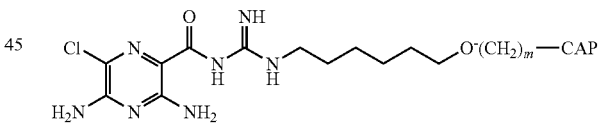

In another preferred embodiment of the present invention the compound of formula (1) is represented by the formula:

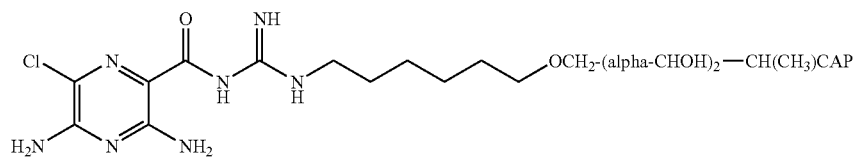

In another preferred embodiment of the present invention the compound of formula (1) is represented by the formula:

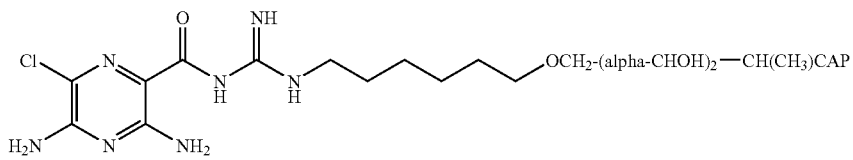

In another preferred embodiment of the present invention the compound of formula (1) is represented by the formula:

In another preferred embodiment of the compound of (1) is represented by the formula:

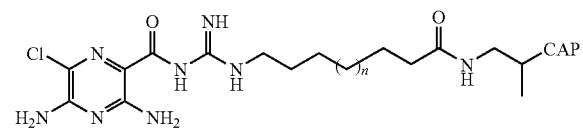

In another preferred embodiment of the present invention the compound of formula (1) is represented by the formula:

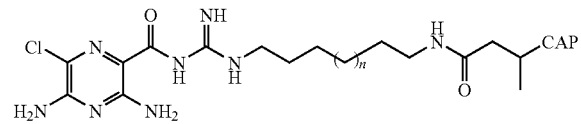

In another preferred embodiment of the present invention the compound of formula (1) is represented by the formula:

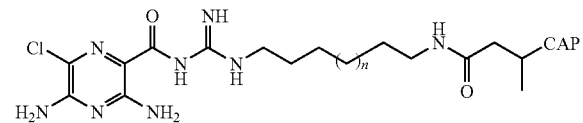

In another preferred embodiment of the present invention the compound of formula (1) is represented by the formula:

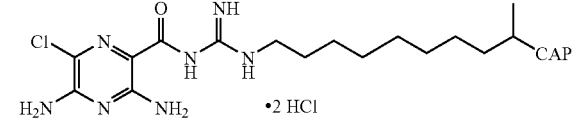

In another preferred embodiment of the present invention the compound of formula (1) is represented by the formula:

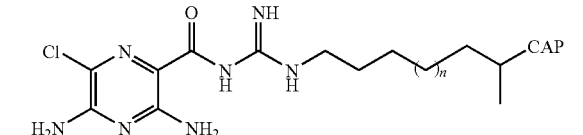

In another preferred embodiment of the present invention the compound of formula (1) is represented by the formula:

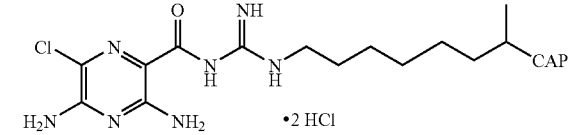

In another preferred embodiment of the present invention the compound of formula (1) is represented by the formula:

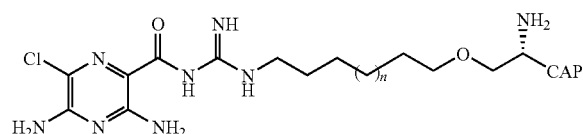

In another preferred embodiment of the present invention the compound of formula (1) is represented by the formula:

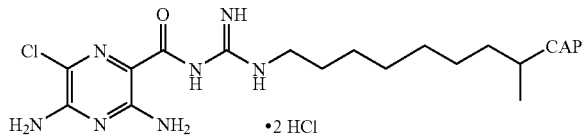

In another preferred embodiment of the present invention the compound of formula (1) is represented by the formula:

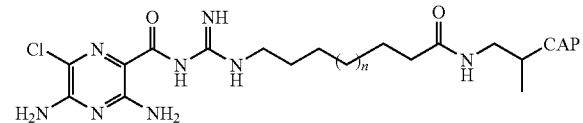

In another preferred embodiment of the present invention the compound of formula (1) is represented by the formula:

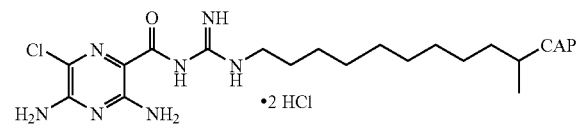

In another preferred embodiment of the present invention the compound of formula (1) is represented by the formula:

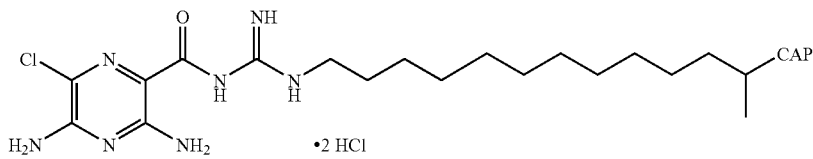

In another preferred embodiment of the present invention the compound of formula (1) is represented by the formula:

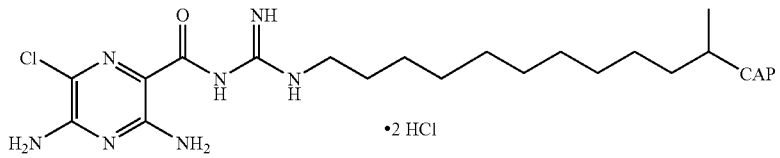

In another preferred embodiment of the present invention the compound of formula (1) is represented by the formula:

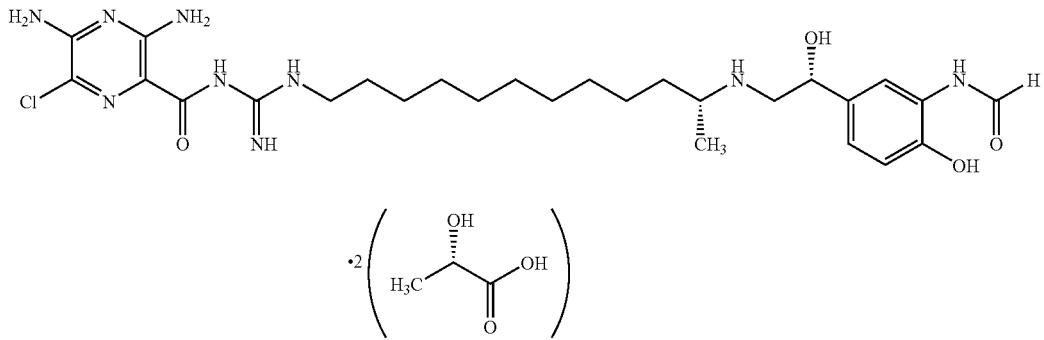

In another preferred embodiment of the present invention the compound of formula (1) is represented by the formula:

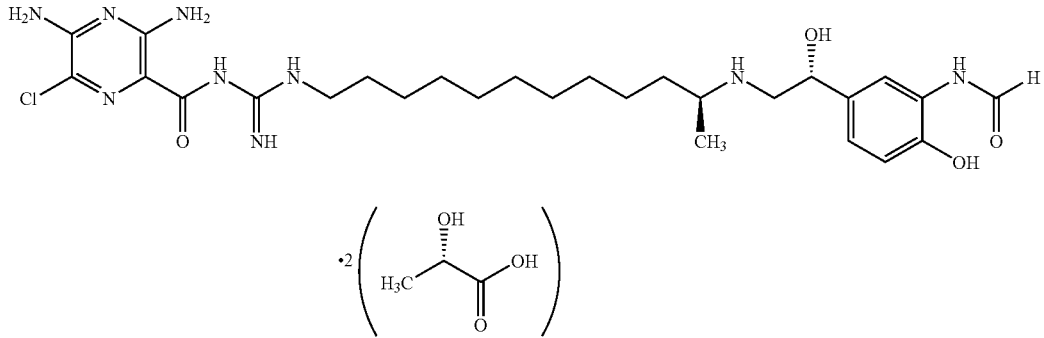

The compounds of formula (I) may be prepared and used as the free base. Alternatively, the compounds may be prepared and used as a pharmaceutically acceptable salt. Pharmaceutically acceptable salts are salts that retain or enhance the desired biological activity of the parent compound and do not impart undesired toxicological effects. Examples of such salts are (a) acid addition salts formed with inorganic acids, for example, hydrochloric acid, hydrobromic acid, sulfuric acid, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid and the like; and (c) salts formed from elemental anions for example, chlorine, bromine, and iodine.

It is to be noted that any of the above compounds can be a pharmaceutically acceptable salt thereof, and wherein the above compounds are inclusive of all racemates, enantiomers, diastereomers, tautomers, polymorphs and pseudopolymorphs thereof. Polymorphs are different physical forms—different crystal forms that have differing melting ranges, show differing differential scanning calorimetry (DSC) tracings and exhibit different X-Ray powder diffraction (XRPD) spectra. Pseudopolymorphs are different solvated physical forms—different crystal forms that have differing melting ranges as solvates, show differing differential scanning calorimetry (DSC) tracings as solvates and exhibit different X-Ray powder diffraction (XRPD) spectra as solvates.

Without being limited to any particular theory, it is believed that the compounds of formula (I) function in vivo as sodium channel blockers and beta receptor agonists. By blocking epithelial sodium channels by activating beta adrenergic receptors present in mucosal surfaces, the compounds of formula (I) reduce the absorption of water by the mucosal surfaces. This effect increases the volume of protective liquids on mucosal surfaces, rebalances the system, and thus treats disease.

The present invention also provides methods of treatment that take advantage of the properties of the compounds of formula (I) discussed above. Thus, subjects that may be treated by the methods of the present invention include, but are not limited to, patients afflicted with cystic fibrosis, primary ciliary dyskinesia, chronic bronchitis, chronic obstructive airway disease, artificially ventilated patients, patients with acute pneumonia, etc. The present invention may be used to obtain a sputum sample from a patient by administering the active compounds to at least one lung of a patient, and then inducing or collecting a sputum sample from that patient. Typically, the invention will be administered to respiratory mucosal surfaces via aerosol (liquid or dry powders or lavage.

Subjects that may be treated by the method of the present invention also include patients being administered supplemental oxygen nasally (a regimen that tends to dry the airway surfaces); patients afflicted with an allergic disease or response (e.g., an allergic response to pollen, dust, animal hair or particles, insects or insect particles, etc.) that affects nasal airway surfaces; patients afflicted with a bacterial infection e.g., staphylococcus infections such as *Staphylococcus aureus* infections, *Hemophilus influenza* infections, *Streptococcus pneumoniae* infections, *Pseudomonas aeuriginosa* infections, etc.) of the nasal airway surfaces; patients afflicted with an inflammatory disease that affects nasal airway surfaces; or patients afflicted with sinusitis (wherein the active agent or agents are administered to promote drainage of congested mucous secretions in the sinuses by administering an amount effective to promote drainage of congested fluid in the sinuses), or combined, Rhinosinusitis. The invention may be administered to rhino-sinal surfaces by topical delivery, including aerosols and drops.

The present invention may be used to hydrate mucosal surfaces other than airway surfaces. Such other mucosal surfaces include gastrointestinal surfaces, oral surfaces, genitourethral surfaces, ocular surfaces or surfaces of the eye, the inner ear and the middle ear. For example, the active compounds of the present invention may be administered by any suitable means, including locally/topically, orally, or rectally, in an effective amount.

The compounds of the present invention are also useful for treating a variety of functions relating to the cardiovascular system. Thus, the compounds of the present invention are useful for use as antihypertensive agents. The compounds may also be used to reduce blood pressure and to treat edema.

In addition, the compounds of the present invention are also useful for promoting diuresis, natriuresis, and saluresis. The compounds may be used alone or in combination with beta blockers, ACE inhibitors, HMGCoA, reductase inhibitors, calcium channel blockers and other cardiovascular agents to treat hypertension, congestive heart failure and reduce cardiovascular mortality.

The compounds of the present invention are also useful for treating airborne infections. Examples of airborne infections include, for example, RSV. The compounds of the present invention are also useful for treating an anthrax infection.

The present invention is concerned primarily with the treatment of human subjects, but may also be employed for the treatment of other mammalian subjects, such as dogs and cats, for veterinary purposes.

As discussed above, the compounds used to prepare the compositions of the present invention may be in the form of a pharmaceutically acceptable free base. Because the free base of the compound is generally less soluble in aqueous solutions than the salt, free base compositions are employed to provide more sustained release of active agent to the lungs. An active agent present in the lungs in particulate form which has not dissolved into solution is not available to induce a physiological response, but serves as a depot of bioavailable drug which gradually dissolves into solution.

Another aspect of the present invention is a pharmaceutical composition, comprising a compound of formula (I) in a pharmaceutically acceptable carrier (e.g., an aqueous carrier solution). In general, the compound of formula (I) is included in the composition in an amount effective to inhibit the reabsorption of water by mucosal surfaces.

The compounds of the present invention may also be used in conjunction with a P2Y2 receptor agonist or a pharmaceutically acceptable salt thereof (also sometimes referred to as an "active agent" herein). The composition may further comprise a P2Y2 receptor agonist or a pharmaceutically acceptable salt thereof (also sometimes referred to as an "active agent" herein). The P2Y2 receptor agonist is typically included in an amount effective to stimulate chloride and water secretion by airway surfaces, particularly nasal airway surfaces. Suitable P2Y2 receptor agonists are described in columns 9-10 of U.S. Pat. No. 6,264,975, U.S. Pat. No. 5,656,256, and U.S. Pat. No. 5,292,498, each of which is incorporated herein by reference.

Bronchodilators can also be used in combination with compounds of the present invention. These bronchodilators include, but are not limited to, anticholinergic agents including but not limited to ipratropium bromide, as well as compounds such as theophylline and aminophylline. These compounds may be administered in accordance with known techniques, either prior to or concurrently with the active compounds described herein.

Another aspect of the present invention is a pharmaceutical formulation, comprising an active compound as described above in a pharmaceutically acceptable carrier (e.g., an aqueous carrier solution). In general, the active compound is included in the composition in an amount effective to treat mucosal surfaces, such as inhibiting the reabsorption of water by mucosal surfaces, including airway and other surfaces.

Ionic and organic osmolytes can also be used in combination with compounds of the present invention. Ionic osmolytes useful include any salt consisting of a pharmaceutically acceptable anion and a pharmaceutical cation. Organic osmolytes include, but are not limited to, sugars, sugar alcohols and organic osmolytes. Detailed examples of ionic and non-ionic osmolytes are given in U.S. Pat. No. 6,926,911 incorporated herein by reference. A particularly useful ionic osmolyte is hypertonic sodium chloride or sodium nitrite. A particularly useful organic osmolyte is the reduced sugar mannitol.

The active compounds disclosed herein may be administered to mucosal surfaces by any suitable means, including topically, orally, rectally, vaginally, ocularly and dermally, etc. For example, for the treatment of constipation, the active compounds may be administered orally or rectally to the gastrointestinal mucosal surface. The active compound may be combined with a pharmaceutically acceptable carrier in any suitable form, such as sterile physiological or dilute saline or topical solution, as a droplet, tablet or the like for oral administration, as a suppository for rectal or genito-urethral administration, etc. Excipients may be included in the formulation to enhance the solubility of the active compounds, as desired.

The active compounds disclosed herein may be administered to the airway surfaces of a patient by any suitable means, including as a spray, mist, or droplets of the active compounds in a pharmaceutically acceptable carrier such as physiological or dilute saline solutions or distilled water. For example, the active compounds may be prepared as formulations and administered as described in U.S. Pat. No. 5,789,391 to Jacobus, the disclosure of which is incorporated by reference herein in its entirety.

Solid or liquid particulate active agents prepared for practicing the present invention could, as noted above, include particles of respirable or non-respirable size; that is, for respirable particles, particles of a size sufficiently small to pass through the mouth and larynx upon inhalation and into the bronchi and alveoli of the lungs, and for non-respirable particles, particles sufficiently large to be retained in the nasal airway passages rather than pass through the larynx and into the bronchi and alveoli of the lungs. In general, particles ranging from about 1 to 5 microns in size (more particularly, less than about 4.7 microns in size) are respirable. Particles of non-respirable size are greater than about 5 microns in size, up to the size of visible droplets. Thus, for nasal administration, a particle size in the range of 10-500 µm may be used to ensure retention in the nasal cavity.

In the manufacture of a formulation according to the invention, active agents or the physiologically acceptable salts or free bases thereof are typically admixed with, inter alia, an acceptable carrier. Of course, the carrier must be compatible with any other ingredients in the formulation and must not be deleterious to the patient. The carrier must be solid or liquid, or both, and is preferably formulated with the compound as a unit-dose formulation, for example, a capsule, that may contain 0.5% to 99% by weight of the active compound. One or more active compounds may be incorporated in the formulations of the invention, which formulations may be prepared by any of the well-known techniques of pharmacy consisting essentially of admixing the components.

Compositions containing respirable or non-respirable dry particles of micronized active agent may be prepared by grinding the dry active agent with a mortar and pestle, and then passing the micronized composition through a 400 mesh screen to break up or separate out large agglomerates.

The particulate active agent composition may optionally contain a dispersant which serves to facilitate the formulation of an aerosol. A suitable dispersant is lactose, which may be blended with the active agent in any suitable ratio (e.g., a 1 to 1 ratio by weight).

Active compounds disclosed herein may be administered to airway surfaces including the nasal passages, sinuses and lungs of a subject by an suitable means know in the art, such as by nose drops, mists, etc. In one embodiment of the invention, the active compounds of the present invention and administered by transbronchoscopic lavage. In a preferred embodiment of the invention, the active compounds of the present invention are deposited on lung airway surfaces by administering an aerosol suspension of respirable particles comprised of the active compound, which the subject inhales. The respirable particles may be liquid or solid. Numerous inhalers for administering aerosol particles to the lungs of a subject are known.

Inhalers such as those developed by Inhale Therapeutic Systems, Palo Alto, Calif., USA, may be employed, including but not limited to those disclosed in U.S. Pat. Nos. 5,740,794; 5,654,007; 5,458,135; 5,775,320; and 5,785,049, each of which is incorporated herein by reference. The Applicant specifically intends that the disclosures of all patent references cited herein be incorporated by reference herein in their entirety. Inhalers such as those developed by Dura Pharmaceuticals, Inc., San Diego, Calif., USA, may also be employed, including but not limited to those disclosed in U.S. Pat. Nos. 5,622,166; 5,577,497; 5,645,051; and 5,492,112, each of which is incorporated herein by reference. Additionally, inhalers such as those developed by Aradigm Corp., Hayward, Calif., USA, may be employed, including but not limited to those disclosed in U.S. Pat. Nos. 5,826,570; 5,813,397; 5,819,726; and 5,655,516, each of which is incorporated herein by reference. These apparatuses are particularly suitable as dry particle inhalers.

Aerosols of liquid particles comprising the active compound may be produced by any suitable means, such as with a pressure-driven aerosol nebulizer or an ultrasonic nebulizer. See, e.g., U.S. Pat. No. 4,501,729, which is incorporated herein by reference. Nebulizers are commercially available devices which transform solutions or suspensions of the active ingredient into a therapeutic aerosol mist either by means of acceleration of compressed gas, typically air or oxygen, through a narrow venturi orifice or by means of ultrasonic agitation. Suitable formulations for use in nebulizers consist of the active ingredient in a liquid carrier, the active ingredient comprising up to 40% w/w of the formulation, but preferably less than 20% w/w. The carrier is typically water (and most preferably sterile, pyrogen-free water) or dilute aqueous alcoholic solution. Perfluorocarbon carriers may also be used. Optional additives include preservatives if the formulation is not made sterile, for example, methyl hydroxybenzoate, antioxidants, flavoring agents, volatile oils, buffering agents and surfactants.

Aerosols of solid particles comprising the active compound may likewise be produced with any solid particulate medicament aerosol generator. Aerosol generators for administering solid particulate medicaments to a subject produce particles which are respirable, as explained above, and generate a volume of aerosol containing predetermined metered dose of medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of powder blend comprising the active ingredient, a suitable powder diluent, such as lactose, and an optional surfactant.

The active ingredient typically comprises of 0.1 to 100% w/w of the formulation. A second type of illustrative aerosol generator comprises a metered dose inhaler. Metered dose inhalers are pressurized aerosol dispensers, typically containing a suspension or solution formulation of active ingredient in a liquified propellant. During use, these devices discharge the formulation through a valve adapted to deliver a metered volume, typically from 10 to 150 μl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one of more co-solvents, for example, ethanol, surfactants, such as oleic acid or sorbitan trioleate, antioxidants and suitable flavoring agents.

The aerosol, whether formed from solid or liquid particles, may be produced by the aerosol generator at a rate of from about 10 to 150 liters per minute, more preferable from 30 to 150 liters per minute, and most preferably about 60 liters per minute. Aerosols containing greater amounts of medicament may be administered more rapidly.

The dosage of the active compounds disclosed herein will vary depending on the condition being treated and the state of the subject, but generally may be from about 0.01, 0.03, 0.05, 0.1 to 1, 5, 10 or 20 mg of the pharmaceutic agent, deposited on the airway surfaces. The daily dose may be divided among one or multiple unit dose administrations. The goal is to achieve a concentration of the pharmaceutic agents on lung airway surfaces of between $10^{-9}$-$10^{4}$ M.

In another embodiment, they are administered by administering an aerosol suspension respirable or non-respirable particles (preferably non-respirable particles) comprised of active compound, which the subject inhales through the nose. The respirable or non-respirable particles may be liquid or solid. The quantity of active agent included may be an amount of sufficient to achieve dissolved concentrations of active agent on the airway surfaces of the subject of from about $10^{-9}$, $10^{-8}$, or $10^{-7}$ to about $10^{-3}$, $10^{-2}$, $10^{-1}$ moles/liter, and more preferably from about $10^{-9}$ to about $10^{-4}$ moles/liter.

The dosage of active compound will vary depending on the condition being treated and the state of the subject, but generally may be an amount sufficient to achieve dissolved concentrations of active compound on the nasal airway surfaces of the subject from about $10^{-9}$, $10^{-8}$, $10^{-7}$ to about $10^{-3}$, $10^{-2}$, or $10^{-1}$ moles/liter, and more preferably from about $10^{-7}$ to about $10^{-4}$ moles/liter. Depending upon the solubility of the particular formulation of active compound administered, the daily dose may be divided among one or several unit dose administrations. The daily dose by weight may range from about 0.01, 0.03, 0.1, 0.5 or 1.0 to 10 or 20 milligrams of active agent particles for a human subject, depending upon the age and condition of the subject. A currently preferred unit dose is about 0.5 milligrams of active agent given at a regimen of 2-10 administrations per day. The dosage may be provided as a prepackaged unit by any suitable means (e.g., encapsulating a gelatin capsule).

In one embodiment of the invention, the particulate active agent composition may contain both a free base of active agent and a pharmaceutically acceptable salt to provide both early release and sustained release of active agent for dissolution into the mucus secretions of the nose. Such a composition serves to provide both early relief to the patient, and sustained relief over time. Sustained relief, by decreasing the number of daily administrations required, is expected to increase patient compliance with the course of active agent treatments.

Pharmaceutical formulations suitable for airway administration include formulations of solutions, emulsions, suspensions and extracts. See generally, J. Nairn, Solutions, Emulsions, Suspensions and Extracts, in Remington: The Science and Practice of Pharmacy, chap. 86 ($19^{th}$ ed. 1995), incorporated herein by reference. Pharmaceutical formulations suitable for nasal administration may be prepared as described in U.S. Pat. Nos. 4,389,393 to Schor; 5,707,644 to Illum; 4,294,829 to Suzuki; and 4,835,142 to Suzuki, the disclosures of which are incorporated by reference herein in their entirety.

Mists or aerosols of liquid particles comprising the active compound may be produced by any suitable means, such as by a simple nasal spray with the active agent in an aqueous pharmaceutically acceptable carrier, such as a sterile saline solution or sterile water. Administration may be with a pressure-driven aerosol nebulizer or an ultrasonic nebulizer. See e.g. U.S. Pat. Nos. 4,501,729 and 5,656,256, both of which are incorporated herein by reference. Suitable formulations for use in a nasal droplet or spray bottle or in nebulizers consist of the active ingredient in a liquid carrier, the active ingredient comprising up to 40% w/w of the formulation, but preferably less than 20% w/w. Typically the carrier is water (and most preferably sterile, pyrogen-free water) or dilute aqueous alcoholic solution, preferably made in a 0.12% to 0.8% solution of sodium chloride. Optional additives include preservatives if the formulation is not made sterile, for example, methyl hydroxybenzoate, antioxidants, flavoring agents, volatile oils, buffering agents, osmotically active agents (e.g. mannitol, xylitol, erythritol) and surfactants.

Compositions containing respirable or non-respirable dry particles of micronized active agent may be prepared by grinding the dry active agent with a mortar and pestle, and then passing the micronized composition through a 400 mesh screen to break up or separate out large agglomerates.

The particulate composition may optionally contain a dispersant which serves to facilitate the formation of an aerosol. A suitable dispersant is lactose, which may be blended with the active agent in any suitable ratio (e.g., a 1 to 1 ratio by weight).

The compounds of formula (I) may be synthesized according to procedures known in the art. A representative synthetic procedure is shown in the scheme below (scheme 1):

These procedures are described in, for example, E. J. Cragoe, "The Synthesis of Amiloride and Its Analogs" (Chapter 3) in *Amiloride and Its Analogs*, pp. 25-36, incorporated herein by reference. Other methods of preparing the compounds are described in, for example, U.S. Pat. No. 3,313,813, incorporated herein by reference. See in particular Methods A, B, C, and D described in U.S. Pat. No. 3,313,813. Other methods useful for the preparation of these compounds, especially for the preparation of the novel $HNR^3R^4$ fragment are described in, for example, U.S. Pat. No. 6,858,614, U.S. Pat. No. 6,858,615, and U.S. Pat. No. 6,903,105, incorporated herein by reference.

Scheme 1-2 are representative of but not limited to, procedures used to prepare the Sodium Channel Blockers/Beta Adrenergic Agonists described herein.

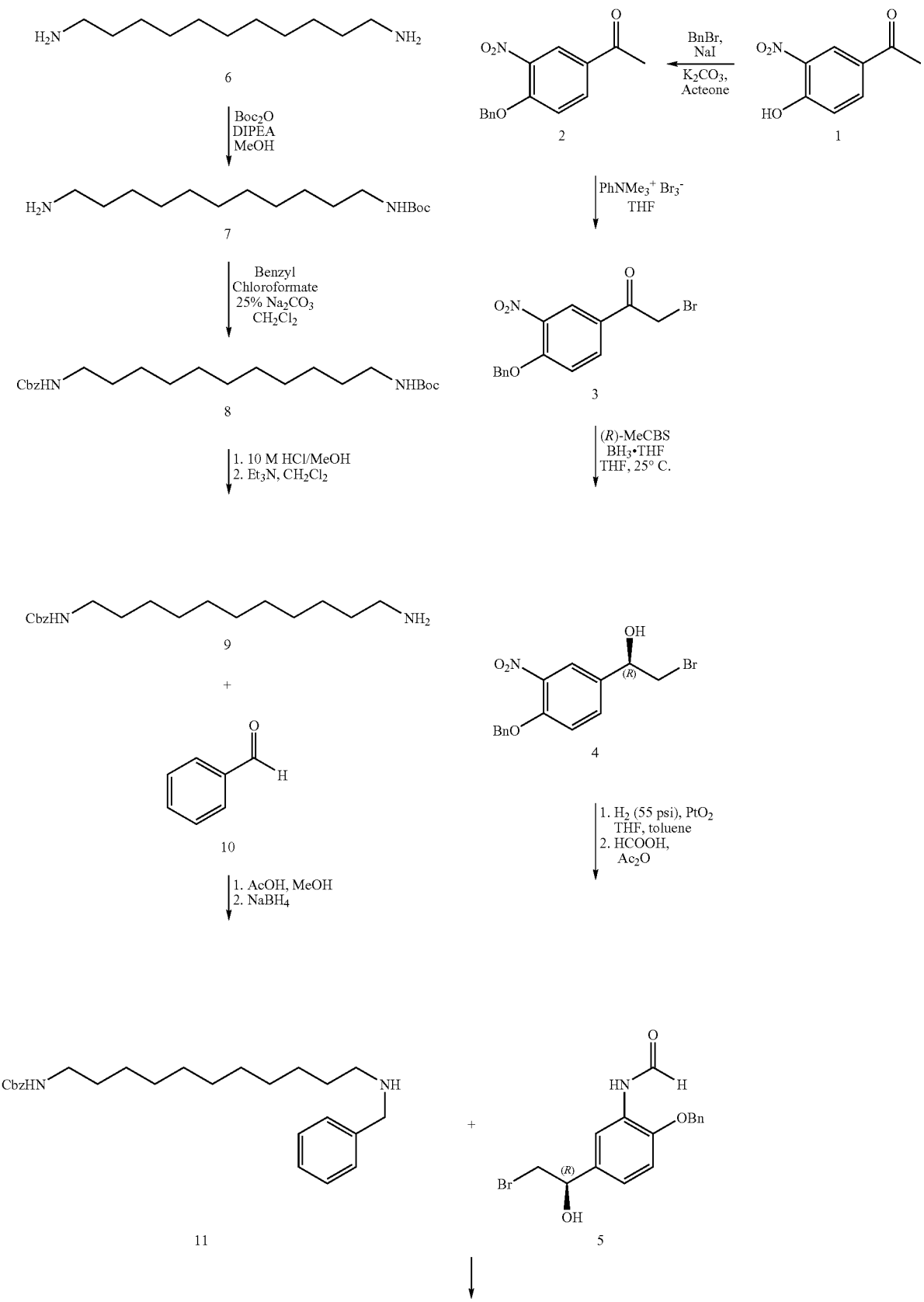
Scheme 1: Synthesis of 15

-continued
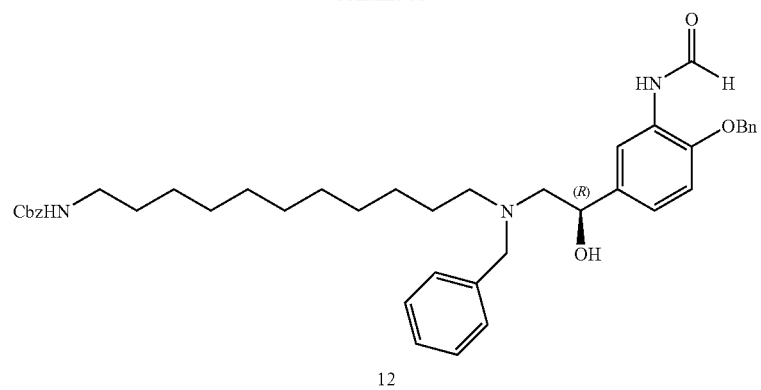
12
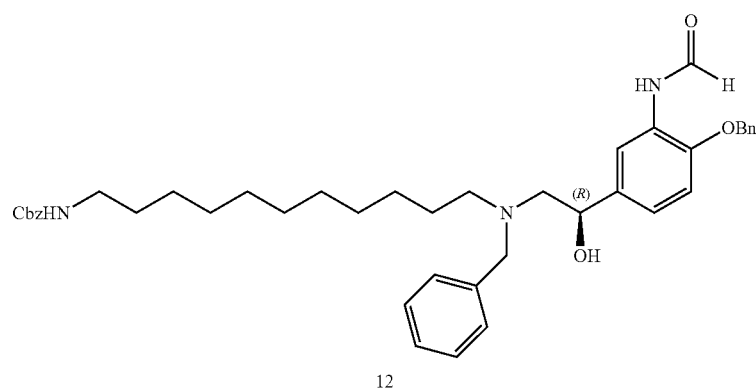
12
| H₂ (1 atm)
| 20% Pd(OH)₂/C
↓ EtOH
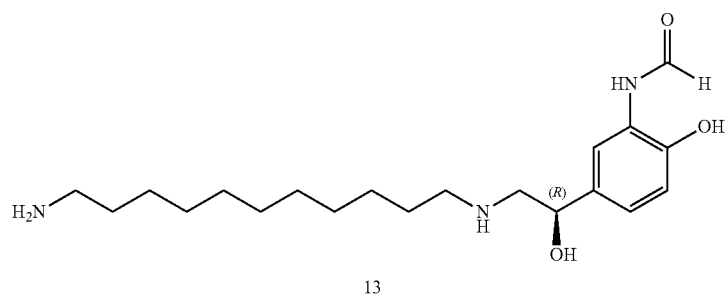
13
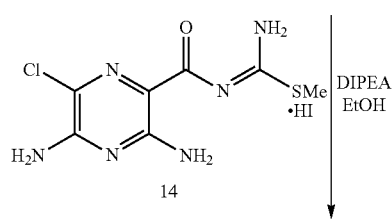
14
DIPEA
EtOH
↓

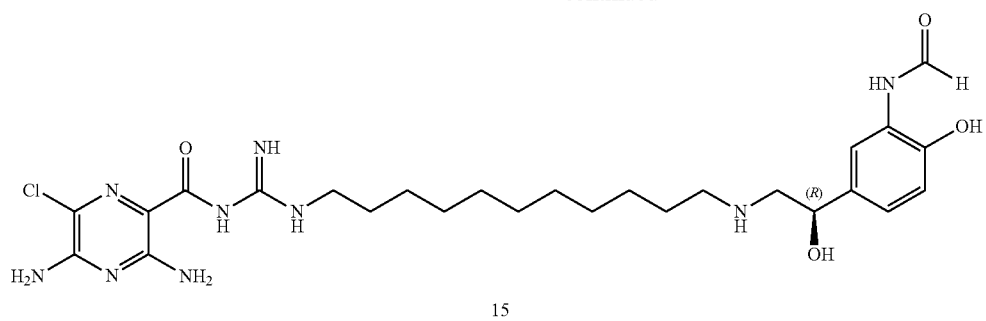
15
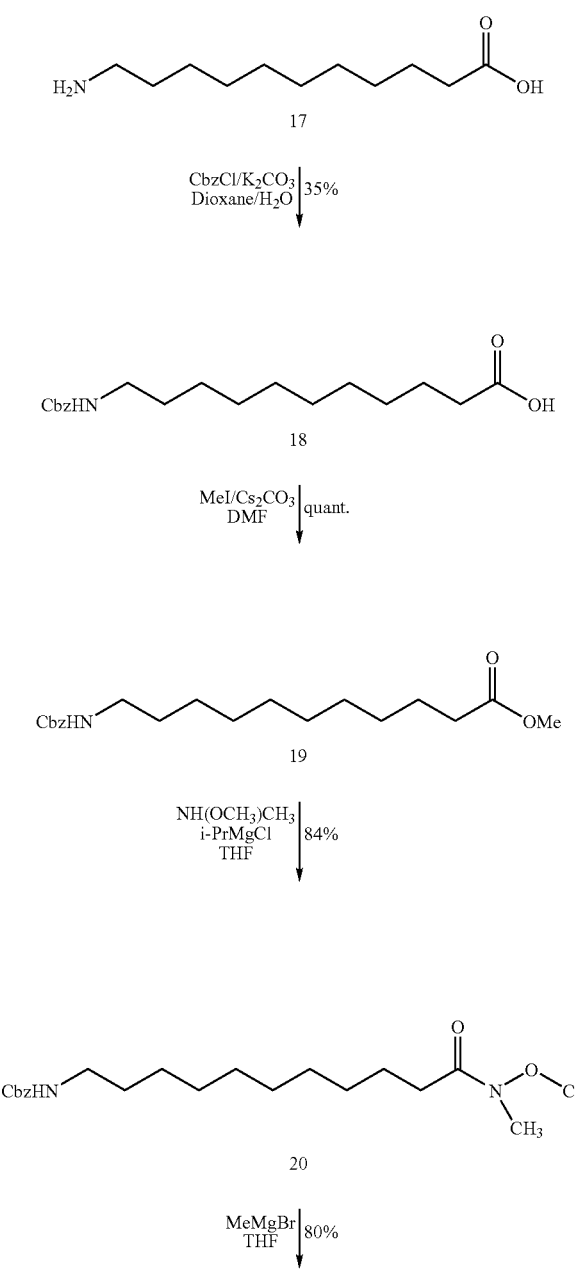
Scheme 2. Synthesis of 26a and 26b

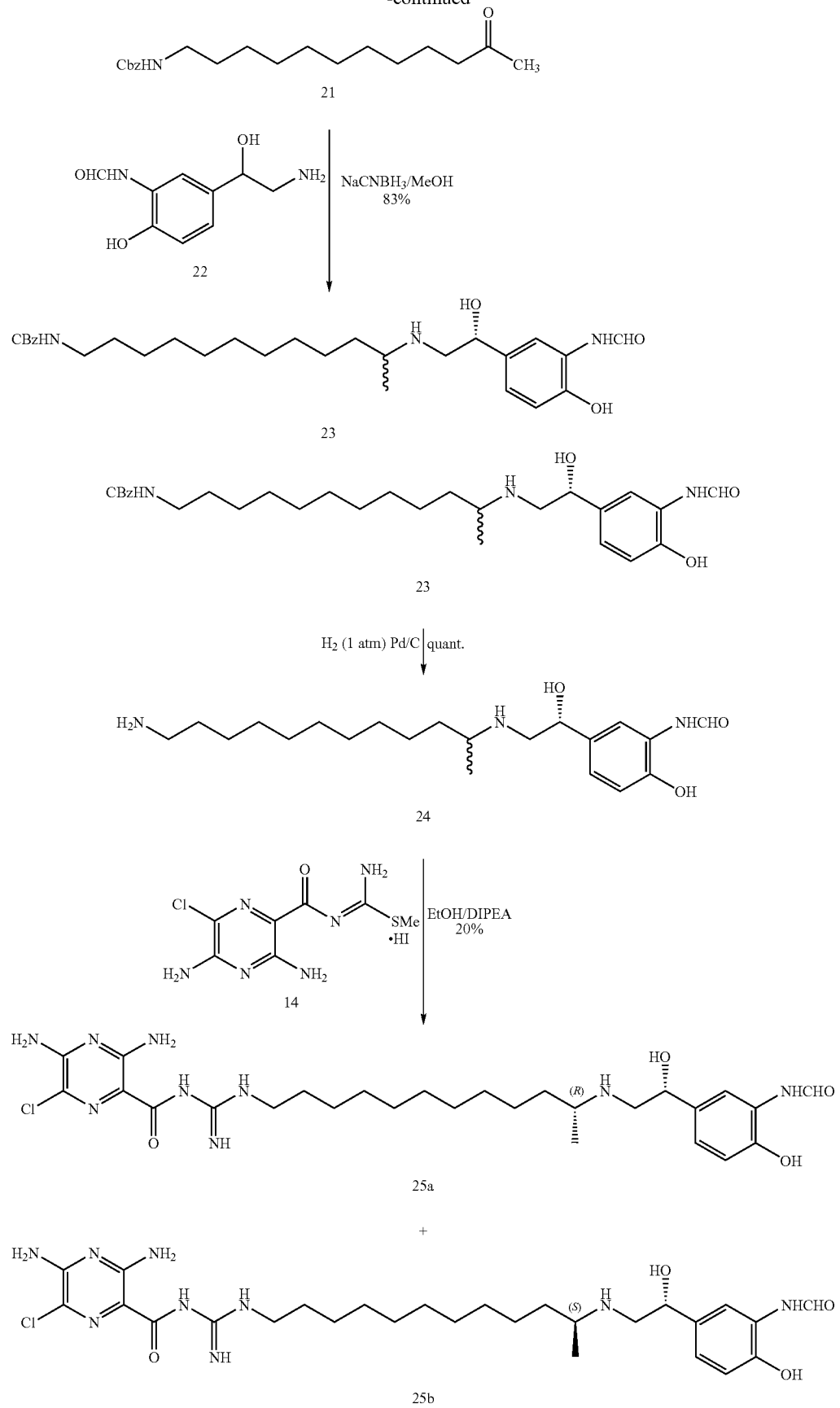

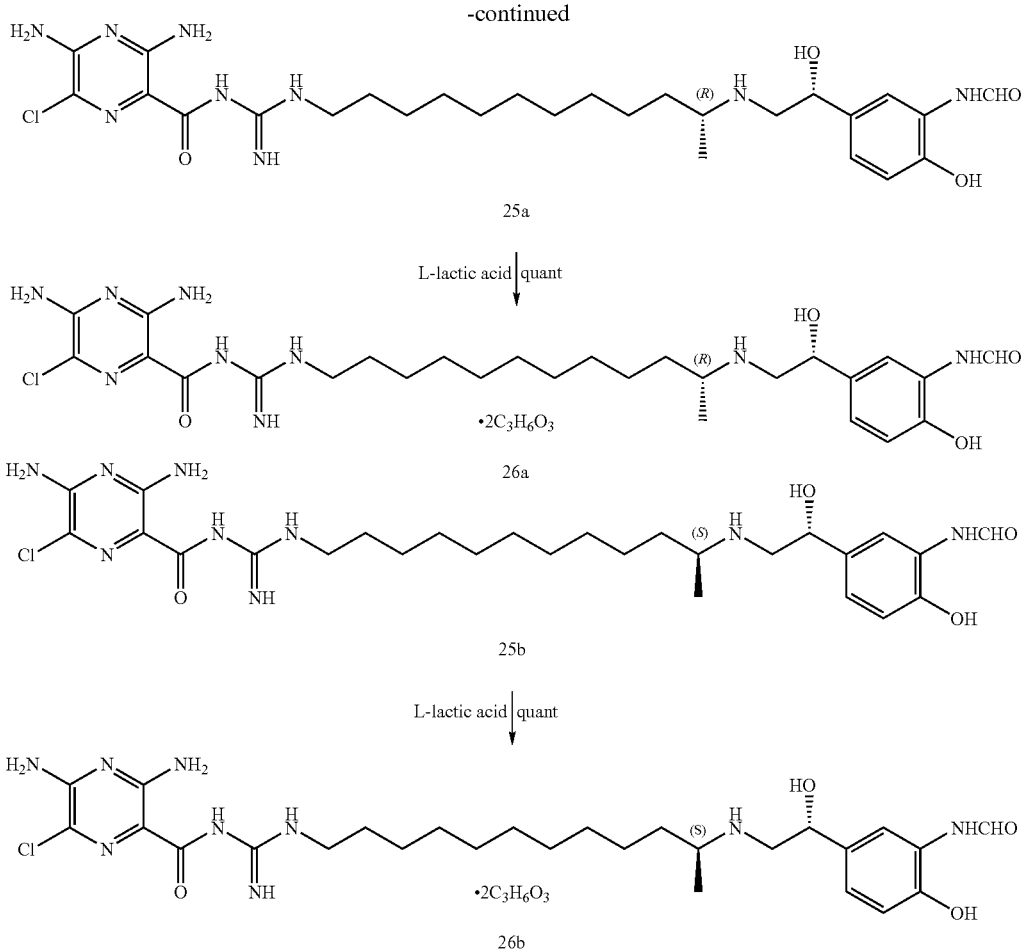

Several assays may be used to characterize the compounds of the sent invention. Representative assays are described below.

1. In Vitro Measure of Epithelial Sodium Channel Block and Beta Agonist Activity To assess the potency of epithelial sodium channel block and beta agonist activity each compound was tested using two separate experimental procedures with similar methodology.

To assess epithelial sodium channel blocker potency the compounds of the present invention involves the determination of lumenal drug inhibition of airway epithelial sodium currents measured under short circuit current ($I_{SC}$) using airway epithelial monolayers mounted in Ussing chambers. Cells obtained from freshly excised human, or dog airways are seeded onto porous 0.4 micrometer Transwell® Permeable Supports (Corning Inc. Acton, Mass.), cultured at air-liquid interface (ALI) conditions in hormonally defined media, and assayed for sodium transport activity ($I_{SC}$) while bathed in Krebs Bicarbonate Ringer (KBR) in Ussing chambers. All test drug additions are to the lumenal bath with approximately half-log dose additions (from $1 \times 10^{-11}$ M to $6 \times 10^{-5}$ M), and the cumulative change in $I_{SC}$ (decreases) recorded. All drugs are prepared in dimethyl sulfoxide as stock solutions at a concentration of approximately $1 \times 10^{-2}$ and stored at $-20°$ C. Six preparations are typically run in parallel; one preparation per run incorporates 552-02 as a positive control. Before the start of the concentration-effect relationship propranolol, a non-selective beta agonist blocker, was applied to the lumenal bath (10 μM) to inhibit the beta agonist component of the designer multiple ligand (DML). All data from the voltage clamps are collected via a computer interface and analyzed off-line.

Concentration-effect relationships for all compounds are considered and analyzed Using GraphPad Prism version 3.00 for Windows, GraphPad Software, San Diego Calif. USA. $IC_{50}$ values, maximal effective concentrations, are calculated and compared to the 552-02 potency as a positive control.

To assess beta agonist activity the compounds of the present invention involves the determination of lumenal drug addition to promote airway epithelial anion currents measured under short circuit current ($I_{SC}$) using airway epithelial monolayers mounted in Ussing chambers. Cells obtained from freshly excised human, dog, or sheep airways are seeded onto porous 0.4 micron Transwell® Permeable Supports (Corning), cultured at air-liquid interface (ALI) conditions in hormonally defined media, and assayed for anion secretion ($I_{SC}$) while bathed in Krebs Bicarbonate Ringer (KBR) in Ussing chambers. All test drug additions are to the lumenal bath with approximately half-log dose additions (from $8 \times 10^{-10}$ M to $6.5 \times 10^{-5}$ M), and the cumulative change in $I_{SC}$ (excitation) recorded. All drugs are prepared in dimethyl sulfoxide as stock solutions at a concentration from $1 \times 10^{-1}$ to $1 \times 10^{-2}$ M and stored at $-20°$ C. Six preparations are typically run in parallel; one preparation per run incorporates either formoterol, salmeterol, or another well recognized beta agonists as a positive control depending on the analog incorporated in the compound being tested. Before the start of the concentration-effect relationship 552-02 a potent sodium channel blocker was applied to the apical surface (1 μM) to eliminate changes in Isc caused by sodium absorption. All data from the voltage clamps are collected via a computer interface and analyzed off-line.

Concentration-effect relationships for all compounds are considered and analyzed Using GraphPad Prism version 3.00 for Windows, GraphPad Software, San Diego Calif. USA. $EC_{50}$ values, maximal effective concentrations, are calculated and compared to either formoterol or salbutamol as the positive control.

2. In Vitro Assay of Compound Absorption and Biotransformation by Airway Epithelia Airway epithelial cells have the capacity to metabolize drugs during the process of transepithelial absorption. Further, although less likely, it is possible that drugs can be metabolized on airway epithelial surfaces by specific ectoenzyme activities. Perhaps more likely as an ecto-surface event, compounds may be metabolized by the infected secretions that occupy the airway lumens of patients with lung disease, e.g. cystic fibrosis. Thus, a series of assays are performed to characterize any compound biotransformation (metabolism or conjugation) that results from the interaction of test compounds with human airway epithelia and/or human airway epithelial lumenal products.

In the first series of assays, the interaction of test compounds in KBR as an "ASL" stimulant are applied to the apical surface of human airway epithelial cells grown in the Transwell® Permeable Supports (Corning), insert system. For most compounds, metabolism or conjugation (generation of new species) is tested for using high performance liquid chromatography (HPLC) to resolve chemical species and the endogenous fluorescence properties of these compounds to estimate the relative quantities of test compound and novel metabolites. For a typical assay, a test solution (1 mL KBR, containing 100 μM n test compound) is placed on the epithelial lumenal surface. Sequential 5 to 600 μl samples are obtained from the lumenal and serosal compartments respectively for HPLC analysis of (1) the mass of test compound permeating from the lumenal to serosal bath and (2) the potential formation of metabolites from the parent compound. From the HPLC data, the rate of and/or formation of novel metabolite compounds on the lumenal surface and the appearance of test compound and/or novel metabolite in the basolateral solution is quantitated based on internal standards. The data relating the chromatographic mobility of potential novel metabolites with reference to the parent compound are also quantitated.

To analyze the potential metabolism of test compounds by CF sputum, a "representative" mixture of expectorated CF sputum obtained from 10 CF patients (under IRB approval) has been collected. The sputum has been be solubilized in a 1:5 mixture of KBR solution with vigorous vortexing, following which the mixture was split into a "neat" sputum aliquot and an aliquot subjected to ultracentrifugation so that a "supernatant" aliquot was obtained (neat=cellular; supernatant=liquid phase). Typical studies of compound metabolism by CF sputum involve the addition of known masses of test compound to "neat" CF sputum and aliquots of CF sputum "supernatant" incubated at 37° C., followed by sequential sampling of aliquots from each sputum type for characterization of compound stability/metabolism by HPLC analysis as described above. As above, analysis of compound disappearance, rates of formation of novel metabolites, and HPLC mobilities of novel metabolites are then performed.

EXAMPLES

Having generally described this invention, a further understanding can be obtained by reference to certain specific examples which are provided herein for purposes of illustration only and are not intended to be limiting unless otherwise specified.

Preparation of Sodium Channel Blockers with Beta Agonist Activity

Materials and methods. All reagents and solvents were purchased from Aldrich Chemical Corp. and used without further purification. NMR spectra were obtained on either a Bruker WM 360 ($^1$H NMR at 360 MHz and $^{13}$C NMR at 90 MHz) or a Bruker AC 300 ($^1$H NMR at 300 MHz and $^{13}$C NMR at 75 MHz). Flash chromatography was performed on a Flash Elute® system from Elution Solution (PO Box 5147, Charlottesville, Va. 22905) charged with a 90 g silica gel cartridge (40M FSO-0110-040155, 32-63 μm) at 20 psi ($N_2$).

GC-analysis was performed on a Shimadzu GC-17 equipped with a Heliflex Capillary Column (Alltech); Phase: AT-1, Length: 10 meters, ID: 0.53 mm, Film: 0.25 micrometers. GC Parameters: Injector at 320° C., Detector at 320° C., FID gas flow: $H_2$ at 40 ml/min., Air at 400 ml/min. Carrier gas: Split Ratio 16:1, $N_2$ flow at 15 $N_2$ velocity at 18 cm/sec. The temperature program is 70° C. for 0-3 min, 70-300° C. from 3-10 min, 300° C. from 10-15 min.

HPLC analysis was performed on a Gilson 322 Pump, detector UV/Vis-156 at 360 nm, equipped with a Microsorb MV C8 column, 100 A, 25 cm. Mobile phase: A=acetonitrile with 0.1% TFA, B=water with 0.1% TFA. Gradient program: 95:5 B:A for 1 min, then to 20:80 B:A over 7 min, then to 100% A over 1 min, followed by washout with 100% A for 11 min, flow rate: 1 ml/min.

Example 1

Synthesis of (R)-3,5-diamino-6-chloro-N—(N-{11-[2-(3-formamido-4-hydroxyphenyl)-2-hydroxyethylamino]undecyl}carbamimidoyl)pyrazine-2-carboxamide (15) (Scheme 1)

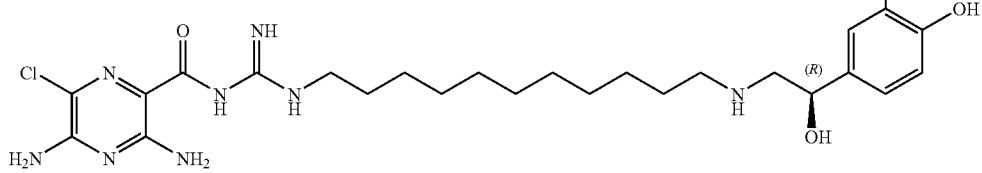

1-(4-Benzyloxy-3-nitrophenyl)ethanone (2)

A mixture of 1-(4-hydroxy-3-nitrophenyl)ethanone (50.00 g, 276 mmol), sodium iodide (20.00 g, 133.4 mmol), potassium carbonate (115.00 g, 832.00 mmol), and benzyl bromide (43.00 mL, 362.00 mmol) in acetone (120 mL) was stirred under reflux for 16 h. The solids were removed by filtration and the filtrate concentrated by rotary evaporation. After this time the resulting residue was diluted with dichloromethane and insoluble inorganics were removed by filtration. The filtrate was concentrated in vacuo and the resulting residue was dissolved in hot chloroform. Hexanes were added to form a precipitate. The solids were collected by filtration to give benzyl ether 2 as a white solid (65.60 g, 87%): $^1$H NMR (500 MHz, CDCl$_3$) δ 2.60 (s, 3H), 5.32 (s, 2H), 7.18 (d, 1H), 7.41 (m, 5H), 8.12 (dd, 1H), 8.44 (d, 1H).

1-(4-Benzyloxy-3-nitrophenyl)-2-bromoethanone (3)

Phenyltrimethylammonium tribromide (109.00 g, 290.00 mmol) was added to a solution of 1-(4-benzyloxy-3-nitrophenyl)ethanone (2) (65.60 g, 242.00 mmol) in anhydrous THF (600 mL) in three portions, and the reaction mixture was stirred at rt for 12 h. The solids were then collected by filtration and the filtrate concentrated. The product was precipitated from chloroform upon the addition of hexanes, then collected by filtration and dried under vacuum to give bromo ketone 3 as a light yellow solid (63.33 g, 75% yield): $^1$H NMR (500 MHz, CDCl$_3$) δ 4.37 (s, 3H), 5.35 (s, 2H), 7.21 (d, 1H), 7.40 (m, 5H), 8.15 (dd, 1H), 8.49 (d, 1H).

1-(4-Benzyloxy-3-nitrophenyl)-2-bromo-1-(R)-ethanol (4)

A solution of BH$_3$.THF in THF (1 M, 108.00 mL, 108.00 mmol) was added to a solution of 1-(4-benzyloxy-3-nitrophenyl)-2-bromoethanone (3) (63.30 g, 180.00 mmol) and R-methyl-CBS-oxazoborolidine (1 M in toluene, 36.00 mL, 36.00 mmol) in anhydrous THF (500 mL). The resulting reaction mixture was stirred at rt for 16 h. Methanol (250 mL) was then slowly added to quench the reaction. After removal of solvent by rotary evaporation, the resulting residue was purified by column chromatography (silica gel, a gradient of 70:30 to 100:0 dichloromethane/hexanes) to give the desired bromo alcohol 4 as a yellow, viscous oil (36.80 g, 75% yield): $^1$H NMR (500 MHz, CDCl$_3$) δ 2.72 (d, 1H), 3.48 (dd, 1H), 3.59 (dd, 1H), 4.89 (m, 1H), 5.21 (s, 2H), 7.11 (d, 1H), 7.39 (m, 5H), 7.50 (dd, 1H), 7.87 (d, 1H).

N-[2-Benzyloxy-5-(2-bromo-1-(R)-hydroxyethyl)phenyl]formamide (5)

A Parr hydrogenator was charged with PtO$_2$ and 1-(4-benzyloxy-3-nitro-phenyl)-2-bromo-1-(R)-ethanol (4) (3.60 g, 10.22 mmol) dissolved in a mixed solvent of THF (25 mL) and toluene (25 mL); and the mixture shaken under an atmosphere of hydrogen at 55 psi at rt for 14 h. The hydrogen pressure was then released. To the mixture was added directly a mixture of formic acid (0.65 mL, 17.23 mmol) and acetic anhydride (1.10 mL, 11.65 mmol). The newly resulting mixture was stirred at rt for an additional 16 h. The catalyst was removed by filtration through a Celite pad and the filtrate was concentrated by rotary evaporation. The resulting residue was purified by column chromatography (silica gel, a gradient of 30:70 to 50:50 ethyl acetate/hexanes) to give the desired formamide 5 as a white solid (3.62 g, >99% yield): $^1$H NMR (300 MHz, CDCl$_3$) δ 2.95 (s, 1H), 3.52 (m, 1H), 3.60 (m, 1H), 4.85 (m, 1H), 5.08 (s, 2H), 6.96 (d, 1H), 7.13 (dd, 1H), 7.39 (m, 5H), 7.88 (br s, 1H), 8.37 (dd, 1H).

tert-Butyl 11-aminoundecylcarbamate (7)

Using a syringe pump, a solution of di-tert-butyl dicarbonate (2.50 g, 11.45 mmol) in methanol (50 mL) was added to a stirred solution of undecane 1,11-diamine (6) (3.00 g, 16.10 mmol) and diisopropylethylamine (2.90 mL, 16.60 mmol) in methanol (200 mL) over 10 h, and the resulting reaction mixture was stirred at rt for 12 h. The reaction was then concentrated to a white solid. Purification by column chromatography (silica gel, 10:90 methanol/dichloromethane, then 20:80 (10% concentrated ammonium hydroxide in methanol)/dichloromethane) afforded the protected amine 7 (2.19 g, 67% yield) as a white solid: $^1$H NMR (300 MHz, CD$_3$OD) δ 1.30 (br s, 14H), 1.43 (br s, 13H), 2.61 (t, 2H), 3.00 (t, 2H).

Benzyl 11-(1-tert-butylamino)undecyl carbamate (8)

Benzylchloroformate (1.30 mL, 9.14 mmol) was added to a mixture of tert-butyl 11-aminoundecylcarbamate (7) (2.19 g, 7.65 mmol) in dichloromethane (40 mL) and 25% sodium carbonate in water (20 mL), and the resulting reaction mixture was stirred at ambient temperature for 3 h. After this time the reaction was extracted with dichloromethane (2×50 mL). The organic extracts combined, concentrated and placed under vacuum. Purification by column chromatography (silica gel, 10:90 methanol/dichloromethane, followed by a gradient of 5:95 to 10:90 (10% concentrated ammonium hydroxide in methanol)/dichloromethane) gave the desired diamine 8 (2.88 g, 92% yield) as a white solid: $^1$H NMR (500 MHz, CDCl$_3$) δ 1.25-1.28 (m, 14H), 1.43-1.55 (m, 13H), 3.09-3.18 (m, 4H), 4.51 (br s, 1H), 4.70 (br s, 1H), 5.09 (s, 2H), 7.22-7.34 (m, 5H); m/z (ESI) 411 [C$_{26}$H$_{38}$N$_2$O$_2$+H]$^+$.

Benzyl 11-aminoundecylcarbamate (9)

Diamine 8 (1.00 g, 2.45 mmol) was dissolved in methanolic hydrogen chloride (10 M, mL) and stirred at ambient temperature for 2 h. After removal of solvent by rotary evaporation, the residue was dissolved in dichloromethane/methanol (2:1, v/v) and triethylamine (0.40 mL, 2.84 mmol) was added. The solution was stirred for 30 min, and then the solvent was removed under vacuum. The residue was carried into the next reaction without purification or characterization.

Benzyl 11-(benzylamino)undecylcarbamate (11)

Benzaldehyde 10 (0.25 mL, 2.47 mmol) was added to a mixture of carbamate 23 (0.76 g, 2.36 mmol), sodium sulfate (100 mg) and ethereal hydrogen chloride (1 M, 2 drops) in dichloroethane (25 mL). The reaction was stirred at ambient temperature for 14 h, then sodium triacetoxyborohydride (0.75 g, 3.54 mmol) was added and stirring continued for an additional 1 h. The reaction was quenched by the addition of saturated aqueous sodium bicarbonate and extracted with dichloromethane (3×25 mL). The combine organics were concentrated under vacuum, then purified by column chromatography (silica, 10:90 (10% concentrated ammonium hydroxide in methanol)/dichloromethane) to give benzylamine 11 (0.44 mg, 59% yield) as a white solid: $^1$H NMR (500 MHz, CD$_3$OD) δ 1.29 (m, 14H), 1.46-1.55 (m, 2H), 2.61 (t, 2H), 3.09 (t, 2H), 3.78 (s, 2H), 4.59 (s, 1H), 5.05 (s, 2H), 7.22-7.34 (m, 10H); m/z (ESI) 411 [C$_{26}$H$_{38}$N$_2$O$_2$+H]$^+$.

(R)-Benzyl 11-(benzyl{2-[4-(benzyloxy)-3-formamidophenyl]-2-hydroxyethyl}-amino)undecylcarbamate (12)

Benzylamine 11 (0.32 g, 0.79 mmol) was added to a suspension of bromoalcohol 19 (0.33 g, 0.95 mmol) and potassium carbonate (0.27 g, 1.98 mmol) in isopropanol (7 mL). The suspension was heated to 83° C. for 40 h. After this time the mixture was cooled, the solid was removed by vacuum filtration and the filtrate was concentrated under vacuum. The resulting yellow solid was subjected to column chromatography (silica, a gradient of 20:80 to 50:50 ethyl acetate/hexanes) to afford the desired product 12 (0.28 g, 52% yield) as a clear oil: $^1$H NMR (300 MHz, CD$_3$OD) δ 1.19-1.72 (m, 18H), 2.48-2.73 (m, 2H), 3.04-3.08 (m, 2H), 3.61-3.84 (m, 2H), 4.66 (t, 1H), 5.04 (br s, 2H), 5.18 (br s, 2H), 6.99-7.67 (m, 18H), 8.22-8.32 (m, 1H);

(R)—N-{5-[2-(11-Aminoundecylamino)-1-hydroxyethyl]-2-hydroxyphenyl}formamide (13)

Aminoalcohol 12 (028 g, 0.41 mmol) was dissolved in ethanol (10 mL). Following the standard hydrogenation procedure, palladium dihydroxide (20% on carbon, 50% wet) was added. The reaction mixture was stirred for 48 h at ambient temperature under atmospheric hydrogen pressure. The catalyst was removed by filtration through diatomaceous earth and the filtrate was concentrated. Drying under vacuum gave 27 (0.12 g, 77% yield) as an orange oil: $^1$H NMR (300 MHz, CD$_3$OD) δ 1.19-1.72 (m, 18H), 2.58-2.89 (m, 4H), 3.51-3.72 (m, 1H), 4.74 (m, 1H), 6.72-6.81 (m, 1H), 6.91-7.06 (m, 1H), 8.02-8.08 (m, 1H), 8.29 (br, 1H).

a solution of amine 14 (116 mg, 0.32 mmol) in ethanol (5 mL). The reaction mixture was heated to 75° C. for 3.5 h. After this time it was cooled and concentrated under vacuum. The resulting residue was purified by column chromatography (silica, a gradient of 10:90 to 80:20 (10% concentrated ammonium hydroxide/methanol)/dichloromethane) affording the crude product. Further purification by prep HPLC [10 to 90% acetonitrile in water (both with 0.01% TFA added) over 40 minutes] and then prep TLC (silica, 10:90 to 30:70 (10% concentrated ammonium hydroxide/methanol)/dichloromethane gave product 15 (26 mg, 14%) as a brown solid: mp 112-116° C.; $^1$H NMR (500 MHz, CD$_3$OD) δ 1.27-1.49 (m, 15H), 1.61-1.74 (m, 4H), 2.91-3.08 (m, 4H), 6.85-6.87 (m, 1H), 7.02-7.05 (m, 1H), 8.01-8.02 (m, 1H), 8.31 (br s, 1H); m/z (ESI) 578 [C$_{26}$H$_{40}$ClN$_9$O$_4$+H]$^+$.

Example 2

Compound 15, ENaC Blocking Activity, IC50 (nM)=27.8 (39× Amiloride)

Beta Agonist Activity, EC50 (nM)=206 (fomoterol=5.3)

Example 3

Compound 16 ENaC Blocking Activity, IC50 (nM)=6.5 (158× Amiloride)

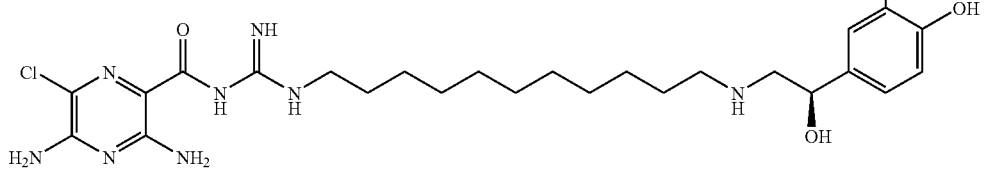

Synthesis of 3,5-diamino-6-chloro-N—(N—((S)-11-(R)-2-(3-formamido-4-hydroxyphenyl)-2-hydroxyethylamino)dodecyl)carbamimidoyl)pyrazine-2-carboxamide di-L-lactate [26a and 26b] (Scheme 2)

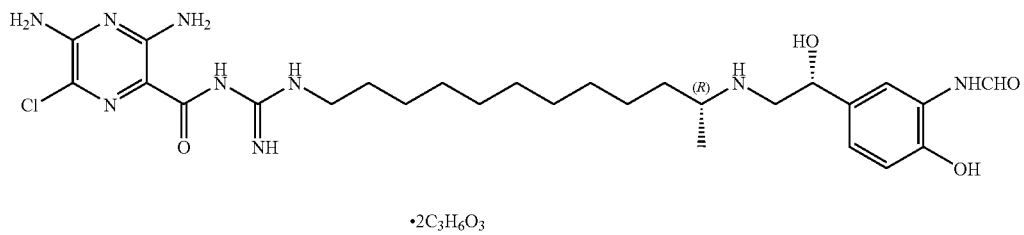

(R)-3,5-Diamino-6-chloro-N—(N-{11-[2-(3-formamido-4-hydroxyphenyl)-2-hydroxyethylamino] undecyl}carbamimidoyl)pyrazinecarboxamide (15)

Diisopropylethylamine (0.07 mL, 0.40 mmol) and 1-(3,5-diamino-6-chloropyrazine-2-carbonyl)-2-methylisothiourea hydriodide (125 mg, 0.32 mmol) were sequentially added to 11-(Benzyloxycarbonylamino)undecanoic acid (18)

To a suspension of 11-aminoundecanoic acid (17) in 1:1 water/dioxane (160 mL total) was added K$_2$CO$_3$ (10.28 g, 74.51 mmol) followed by the slow addition over 30 min of benzylchloroformate (CbzCl, 4.55 mL, 32.29 mmol), and the mixture was stirred at room temperature for 2 h. The solid was then removed by filtration, washed with water (3×30 mL) and dried in a vacuum oven at 40° C. for 72 h to afford a white solid 18 (2.91 g, 35% yield): $^1$H NMR (500 MHz, CD$_3$OD) δ 1.36 (m, 12H), 1.50 (m, 2H), 1.62 (m, 2H), 2.18 (m, 2H), 3.08 (m, 2H), 5.14 (s, 2H), 7.38 (m, 5H); m/z (ESI) 336 [M+H]$^+$.

Methyl 11-(benzyloxycarbonylamino)undecanoate (19)

A suspension of 18 (2.91 g, 8.68 mmol), Cs$_2$CO$_3$ (4.25 g, 13.02 mmol) and DMF (anhydrous, 40 mL) was stirred at room temperature for 1.5 h. To the mixture was then added methyl iodide (0.83 mL, 13.02 mmol), and stifling was continued for an additional 3 h at the ambient temperature. The mixture was then partitioned between water (150 mL) and dichloromethane (150 mL), aqueous layer was separated and washed with dichloromethane (3×300 mL). Organics were combined, dried over anhydrous Na$_2$SO$_4$, concentrated and further dried under high vacuum overnight to afford the desired methyl ester 19 (3.41 g, quant yield): $^1$H NMR (500 MHz, CDCl$_3$) δ 1.26 (m, 12H), 1.47 (m, 2H), 1.52 (m, 2H), 2.28 (m, 2H), 3.16 (m, 2H), 3.66 (s, 3H), 5.10 (s, 2H), 7.32 (m, 5H); m/z (ESI) 350 [M+H]$^+$.

Benzyl 11-(methoxy(methyl)amino)-11-oxoundecylcarbamate (20)

A solution of 19 (2.25 g, 6.44 mmol), methyl methoxyamine hydrochloride (1.26 g, 12.88 mmol) and THF (anhydrous, 30 mL) was cooled to −15 to −20° C. with an ice/methanol bath containing a few pieces of dry ice. To this cold solution was added dropwise i-PrMgCl (3M solution in pentane, 11.27 mL, 22.54 mmol) over 15 min and temperature was then raised to −10° C. and stirring continued at the temperature for additional 2 h. After this time the reaction was quenched by the slow addition of saturated aqueous NH$_4$Cl (50 mL). The aqueous layer was separated and washed with dichloromethane (2×50 mL). Organics were combined, dried over anhydrous Na$_2$SO$_4$, concentrated and further dried under high vacuum overnight to afford the desired product 20 (2.04 g, 84% yield) as a colorless, viscous oil: $^1$H NMR (300 MHz, CDCl$_3$) δ 1.27 (m, 12H), 1.48 (m, 2H), 1.60 (m, 2H), 2.40 (m, 2H), 3.18 (m, 5H), 3.68 (s, 3H), 5.09 (s, 2H), 7.34 (m, 5H); m/z (ESI) 379 [M+H]$^+$.

Benzyl 11-oxododecylcarbamate (21)

To a solution of 20 (1.11 g, 2.94 mmol) in THF (anhydrous, 10 mL) and cooled in an ice bath was added dropwise MeMgCl (3 M solution in diethyl ether, 3.92 mL, 11.75 mmol) over 10 min, and stirring continued at 0° C. for 6 h. The reaction was quenched by the slow addition of methanol (10 mL), and then concentrated under vacuum. The residue was chromatographed (silica gel, a gradient of 0:100 to 18:82 ethyl acetate/hexanes) to afford the desired product 21 (0.78 g, 80% yield) as a white solid: $^1$H NMR (300 MHz, CDCl$_3$) δ 1.26 (m, 12H), 1.49-1.57 (m, 4H), 2.13 (s, 3H), 2.41 (m, 2H), 3.19 (m, 5H), 5.09 (s, 2H), 7.34 (m, 5H); m/z (ESI) 334 [M+H]$^+$.

(R)-Benzyl 11-(2-(3-formamido-4-hydroxyphenyl)-2-hydroxyethylamino)dodecyl-carbamate (23)

A solution containing compound 19 (0.43 g, 1.29 mmol) and (R)—N-(5-(2-amino-1-hydroxyethyl)-2-benzyloxy) phenyl)formamide 22 (0.27 g, 1.35 mmol) in methanol (anhydrous, 6 mL) was stirred at room temperature for 4 h. To this solution was then added NaCNBH$_3$ (0.24 g, 3.87 mmol) in one portion, and the mixture was continuously stirred at room temperature overnight. After this time, the mixture was concentrated and the residue was subjected to chromatography (a gradient of 0:100 to 10:90 methanol/dichloromethane) to afford the desired product 23 (0.54 g, 82% yield): $^1$H NMR (300 MHz, CD$_3$OD) δ 1.31 (m, 15H), 1.48-1.58 (m, 4H), 1.75 (m, 2H), 3.10 (m, 5H), 4.83 (m, 1H), 5.09 (s, 2H), 6.89 (d, 1H), 7.04 (d, 1H), 7.34 (m, 6H), 8.12 (s, 1H), 8.32 (s, 1H); m/z (ESI) 514 [M+H]$^+$.

(R)—N-(5-(2-(12-Aminododecan-2-ylamino)-1-hydroxyethyl)-2-hydroxyphenyl)-formamide (24)

A mixture of compound 23 (0.54 g, 1.05 mmol) dissolved in methanol (30 mL) and palladium catalyst (0.15 g, 10% Pd on carbon, 50% we) was stirred overnight at room temperature under one atmospheric hydrogen pressure. The catalyst was removed by filtration and washed with methanol (3×10 mL). The filtrate and washings were combined and concentrated under vacuum to complete dryness, affording the desired product 24 (0.40 g, 91% yield) as an off-white solid: $^1$H NMR (300 MHz, CD$_3$OD) δ 1.31 (m, 15H), 1.48-1.58 (m, 4H), 1.75 (m, 2H), 260-2.80 (m, 5H), 4.66 (m, 1H), 5.09 (s, 2H), 6.82 (d, 1H), 7.00 (d, 1H), 8.02 (s, 1H), 8.30 (s, 1H); m/z (ESI) 380 [M+H]$^+$.

3,5-Diamino-6-chloro-N—(N—((R)-11-((R)-2-(3-formamide-4-hydroxyphenyl)-2-hydroxyethylamino) dodecyl)carbamimidoyl)pyrazine-2-carboxamide (25a) and 3,5-Diamino-6-chloro-N—(N—((S)-11-(R)-2-(3-formamide-4-hydroxyphenyl)-2-hydroxyethylamine)dodecyl)carbamimidoyl)pyrazine-2-carboxamide (25b)

A suspension of compound 24 (0.40 g, 1.05 mmol), Hunig's base (0.89 mL, 5.27 mmol) and ethanol (14 mL) was heated at 70° C. for 30 min, and then 1-(3,5-diamino-6-chloropyrazine-2-carbonyl)-2-methylisothiourea hydriodide (0.43, 1.17 mmol) was added. The resulting solution was continuously stirred at that temperature for an additional 3 h before it was cooled to room temperature. The un-dissolved solid was removed by filtration, and the filtrate was concentrated. The resulting residue was subjected to column chromatography eluting with a mixture of methanol (0-16%), concentrated ammonium hydroxide (0-1.6%) and dichloromethane (100-83.4%) to afford a mixture of 25a and 25b (0.12 g total, 20% overall yield): $^1$H NMR (500 MHz, CD$_3$OD) δ 1.12 (m, 6H), 1.38-1.50 (m, 30H), 1.57 (m, 4H), 1.73 (m, 4H), 2.72-2.90 (m, 6H), 3.33 (m, 4H), 4.60-4.70 (m, 2H), 6.84 (d, 2H), 7.04 (d, 2H), 8.10 (s, 2H), 8.30 (s, 2H); m/z (ESI) 592 [M+H]$^+$. This material was subjected to further chromatography by prep TLC plates eluting several times with a mixture of methanol (0-22%), concentrated ammonium hydroxide (0-2.2%) and dichloromethane (100-75.8%) to afford 25a (42 mg) and 256 (56 mg), respectively, both as yellow solids. The stereochemistry of the chiral methyl groups in 68a and 69a were arbitrarily assigned.

3,5-Diamino-6-chloro-N—(N—((R)-11-(R)-2-((3-formamido-4-hydroxyphenyl)-2-hydroxyethylamino) dodecyl)carbamimidoyl)pyrazine-2-carboxamide di-L-lactate [26a]

L-lactic acid (13.7 mg, 0.14 mmol) was added to a suspension of compound 25a (42 mg, 0.15 mmol) in absolute ethanol (3 mL). The mixture was stirred at room temperature for 1 h and turned to a clear solution. The solution was then concentrated under vacuum and completely dried to afford 26a (46 mg, quant yield) as a brown, viscous oil: $^1$H NMR (500 MHz, DMSO-$d_6$) δ 1.18-1.24 (m, 21H), 1.40-1.75 (m, 6H), 2.96 (m, 2H), 3.07 (m, 1H), 3.28 (m, 2H), 4.10 (m, 2H), 4.82 (m, 1H), 6.08 (br s, 1H), 6.84 (d, 1H), 7.04 (d, 1H), 7.48 (br s, 2H), 8.16 (s, 1H), 8.30 (s, 1H), 8.88-9.10 (br s, 2H), 9.66 (s, 1H), 9.96 (br s, 1H); m/z (ESI) 592 [M+H]$^+$.

3,5-Diamino-6-chloro-N—(—((S)-11-(R)-2-((3-formamide-4-hydroxyphenyl)-2-hydroxyethylamino)dodecyl)carbamimidoyl)pyrazine-2-carboxamide di-L-lactate [26b]

Compound 26b (44 mg, quant yield), a brown solid, was prepared from 25b in a similar method to 68a: mp 86-88° C. (decomposed); $^1$H NMR (500 MHz, DMSO-$d_6$) δ 1.11 (d, 3H), 1.20 (s, 6H), 1.28-1.36 (m, 12H), 1.48-1.70 (m, 6H), 2.78-3.26 (m, 5H), 3.92 (m, 2H), 4.64 (m, 1H), 6.72-6.82 (br s, 2H), 6.84 (d, 1H), 6.92 (d, 1H), 8.09 (s, 1H), 8.28 (s, 1H), 9.59 (br s, 1H); m/z (ESI) 592 [M+H]$^+$.

Methods
Pharmacological Effects and Mechanism of Action of the Drug in Animals

The effect of compounds for enhancing mucociliary clearance (MCC) can be measured using an in vivo model described by Sabater et al., Journal of Applied Physiology, 1999, 87(6) pp. 2191-2196, incorporated herein by reference.

Animal Preparation: Adult ewes up to 75 Kg were placed in a restrain and positioned upright using a specialized body harness. The heads of the animals were immobilized, and local anesthesia of the nasal passage was provided (2% lidocaine) prior to nasal intubation (7.5 mm-I.D. endotracheal tube (ETT) (Mallinckrodt Medical, St. Louis, Mo.). The cuff of the ETT was placed just below the vocal cords. After intubation, the animals were allowed to equilibrate for approximately 20 min before MCC measurements began.

Sheep MCC in vivo Measurement: Aerosols of sulfur colloid radiolabled with technetium ($^{99m}$Tc—SC 3.1 mg/mL, ~10-15 mCi) were generated by a Raindrop Nebulizer (Nellcor Puritan Bennett, Pleasanton, Calif.) which produces a median aerodynamic droplet diameter of 3.6 μm. The nebulizer was connected to a dosimeter system consisting of a solenoid valve and a source of compressed air (20 psi). The output of the nebulizer was directed into a T piece, with one end attached to a respirator (Harvard apparatus, South Natick, Mass.). The system was activated for 1 second at the onset of the respirator's inspiratory cycle. The tidal volume was set at 300 mL, with an inspiratory-to-expiratory ratio of 1:1, and a rate of 20 breaths/min, to maximize central airway deposition. The sheep breathed the $^{99m}$Tc—SC aerosol for up to 5 min. Following tracer deposition, a gamma camera was used to measure the clearance of $^{99m}$Tc—SC from the airways. The camera was positioned above the animal's back with the sheep in its natural upright position in the harness. The field of the image was perpendicular to the animal's spinal cord. External radiolabled markers were placed on the sheep to facilitate proper alignment of the gamma camera. A region of interest was traced over the image corresponding to the right lung of the sheep and counts were recorded. The counts were corrected for decay and expressed as a percentage of radioactivity present in the baseline image. The left lung was excluded from the analysis because the outline of the lung was superimposed over the stomach and counts could be affected by swallowed $^{99m}$Tc—SC-labeled mucus. All deposition images were stored on a computer interfaced to the gamma camera. The protocol included a baseline deposition image obtained immediately post radio-aerosol administration. After acquisition of baseline images, either 4 mL of $H_2O$ (vehicle), formoterol (3 mM), or novel chemical entity (3 mM) were aerosolized using the Pari LC JetPlus nebulizer to free-breathing sheep using two separate protocols. Protocol 1, acquired data immediately after dosing (time 0 to 1 hour), and indicated the immediate physiological response 'short-term efficacy' protocol 2, acquired data 4 hours post dosing indicated compound durability and 'long-term efficacy'. The nebulizer had a flow rate of 8 L/min and the time to deliver the solution was 10-12 min. On the completion of compound administration, the animal was immediately extubated to prevent false elevations in counts due to aspiration of excess $^{99m}$Tc—SC-labeled mucus from the ETT. Serial measurements of $^{99m}$Tc—SC retained in the lung were obtained over a 1 hour period at 5 min intervals. A washout period of at least 7 days (half life of $^{99m}$TC=6 h) separated studies with the different agents.

Statistical Analysis: Data from the in vivo sheep MCC assays were analyzed using a two way ANOVA with repeated measures, followed by slope analysis of the linear regression of the retention vs time plot using an ANOCOVA to compare slopes, and if needed a multiple comparison test (Newman-Keuls). The percent activity retained (post 4 hours) was calculated by dividing the slope value from protocol 2 by the slope value obtained in protocol 1 and multiplying by 100%.

Animal Preparation: Adult ewes (ranging in weight from 25 to 35 kg) were restrained in an upright position in a specialized body harness adapted to a modified shopping cart. The animals' heads were immobilized and local anesthesia of the nasal passage was induced with 2% lidocaine. The animals were then nasally intubated with a 7.5 mm internal diameter endotracheal tube (ETT). The cuff of the ETT was placed just below the vocal cords and its position was verified with a flexible bronchoscope. After intubation the animals were allowed to equilibrate for approximately 20 minutes prior to initiating measurements of mucociliary clearance.

Administration of Radio-aerosol: Aerosols of $^{99m}$Tc-Human serum albumin (3.1 mg/ml; containing approximately 20 mCi) were generated using a Raindrop Nebulizer which produces a droplet with a median aerodynamic diameter of 3.6 p.m. The nebulizer was connected to a dosimetry system consisting of a solenoid valve and a source of compressed air (20 psi). The output of the nebulizer was directed into a plastic T connector; one end of which was connected to the endotracheal tube, the other was connected to a piston respirator. The system was activated for one second at the onset of the respirator's inspiratory cycle. The respirator was set at a tidal volume of 500 mL, an inspiratory to expiratory ratio of 1:1, and at a rate of 20 breaths per minute to maximize the central airway deposition. The sheep breathed the radio-labeled aerosol for 5 minutes. A gamma camera was used to measure the clearance of $^{99m}$Tc-Human serum albumin from the airways. The camera was positioned above the animal=s back with the sheep in a natural up ht position supported in a cart so that the field of image was perpendicular to the animal=s spinal cord. External radio-labeled markers were placed on the sheep to ensure proper alignment under the gamma camera. All images were stored in a computer integrated with the gamma camera. A region of interest was traced over the image corresponding to the right lung of the sheep and the counts were recorded. The counts were corrected for decay and expressed as percentage of radioactivity present in the initial baseline image. The left lung was excluded from the analysis because its outlines are superimposed over the stomach and counts can be swallowed and enter the stomach as radio-labeled mucus.

Treatment Protocol (Assessment of activity at t-zero): A baseline deposition image was obtained immediately after radio-aerosol administration. At time zero, after acquisition of the baseline image, vehicle control (distilled water), positive control (amiloride), or experimental compounds were aerosolized from a 4 ml volume using a Pari LC JetPlus nebulizer to free-breathing animals. The nebulizer was driven by compressed air with a flow of 8 liters per minute. The time to deliver the solution was 10 to 12 minutes. Animals were extubated immediately following delivery of the total dose in order to prevent false elevations in counts caused by aspiration of excess radio-tracer from the ETT. Serial images of the lung were obtained at 15-minute intervals during the first 2 hours after dosing and hourly for the next 6 hours after dosing for a total observation period of 8 hours. A washout period of at least 7 days separated dosing sessions with different experimental agents.

Treatment Protocol (Assessment of Activity at t-4 hours): The following variation of the standard protocol was used to assess the durability of response following a single exposure to vehicle control (distilled water), positive control compounds (amiloride or benzamil), or investigational agents. At time zero, vehicle control (distilled water), positive control (amiloride), or investigational compounds were aerosolized from a 4 ml volume using a Pari LC JetPlus nebulizer to free-breathing animals. The nebulizer was driven by compressed air with a flow of 8 liters per minute. The time to deliver the solution was 10 to 12 minutes. Animals were restrained in an upright position in a specialized body harness for 4 hours. At the end of the 4-hour period animals received a single dose of aerosolized $^{99m}$Tc-Human serum albumin (3.1 mg/ml; containing approximately 20 mCi) from a Raindrop Nebulizer. Animals were extubated immediately following delivery of the total dose of radio-tracer. A baseline deposition image was obtained immediately after radio-aerosol administration. Serial images of the lung were obtained at 15-minute intervals during the first 2 hours after administration of the radio-tracer (representing hours 4 through 6 after drug administration) and hourly for the next 2 hours after dosing for a total observation period of 4 hours. A washout period of at least 7 days separated dosing sessions with different experimental agents.

Statistics: Data were analyzed using SYSTAT for Windows, version 5. Data were analyzed using a two-way repeated ANOVA (to assess overall effects), followed by a paired t-test to identify differences between specific pairs. Significance was accepted when P was less than or equal to 0.05. Slope values (calculated from data collected during the initial 45 minutes after dosing in the t-zero assessment) for mean MCC curves were calculated using linear least square regression to assess differences in the initial rates during the rapid clearance phase.

Obviously, numerous modifications and variations of the present invention are possible in light of the above teachings. It is therefore to be understood that within the scope of the appended claims, the invention may be practiced otherwise than as specifically described herein.

The invention claimed is:

1. A compound which is represented by the formula:

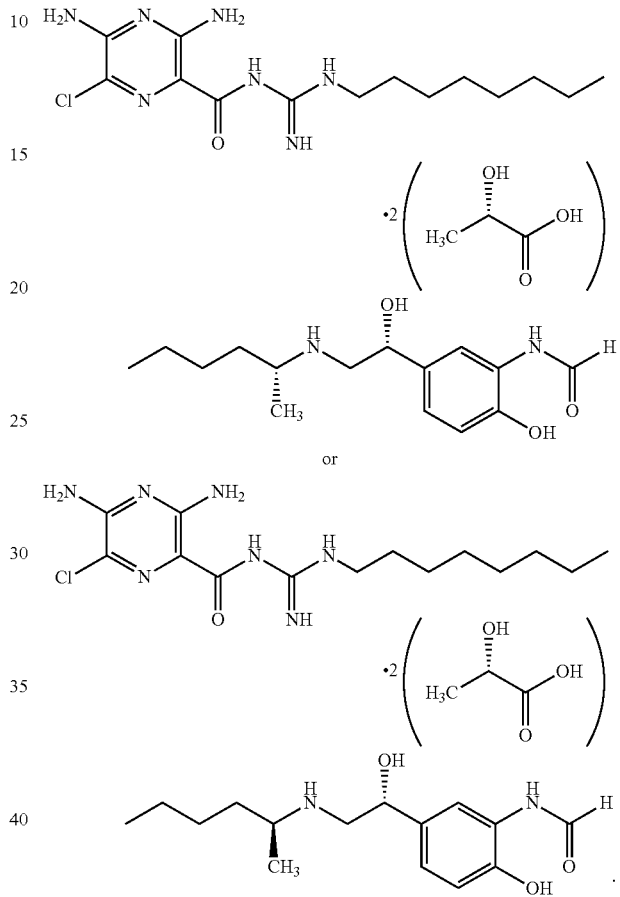

2. A pharmaceutical composition comprising a compound of claim 1 and a pharmaceutically acceptable carrier.

3. A method of blocking sodium channels and activating beta receptors simultaneously, comprising contacting sodium channels and beta receptors with an effective amount of a compound of claim 1.

* * * * *